US008263401B2

(12) United States Patent
Vatner et al.

(10) Patent No.: US 8,263,401 B2
(45) Date of Patent: Sep. 11, 2012

(54) ADENYLYL CYCLASE ANTIBODIES, COMPOSITIONS AND USES THEREOF

(75) Inventors: Stephen F. Vatner, Barnegat Light, NJ (US); Dorothy E. Vatner, Barnegat Light, NJ (US); Junichi Sadoshima, Berkeley Heights, NJ (US); Jayashree Pain, Livingston, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 924 days.

(21) Appl. No.: 11/597,065

(22) PCT Filed: May 26, 2005

(86) PCT No.: PCT/US2005/018589
§ 371 (c)(1), (2), (4) Date: May 6, 2008

(87) PCT Pub. No.: WO2005/115121
PCT Pub. Date: Dec. 8, 2005

(65) Prior Publication Data
US 2008/0274103 A1 Nov. 6, 2008

(51) Int. Cl.
C12N 5/20 (2006.01)
C07K 16/40 (2006.01)
C07H 7/00 (2006.01)
(52) U.S. Cl. ............ 435/326; 435/338; 530/388.26
(58) Field of Classification Search .................. None
See application file for complete search history.

(56) References Cited

U.S. PATENT DOCUMENTS

| 5,334,512 A | 8/1994 | Kobayashi et al. | |
|---|---|---|---|
| 2005/0019809 A1* | 1/2005 | Storm et al. .................. | 435/6 |

FOREIGN PATENT DOCUMENTS

| EP | 0529662 A2 | 3/1993 |
|---|---|---|
| WO | WO 93/05061 | 3/1993 |

OTHER PUBLICATIONS

Asboth et al (Reproduction, 2001, 121(2): 217-228).*
Moorman and Plasterk (Genetics 2002, 161: 133-142).*
Hurley (J. Biol. Chem. 1999, 274(2): 7599-7602).*
Baughman, K. "New Medical Therapies for Advanced Left Ventricular Dysfunction" Cardiology Clinics 1995 13(1):27-34.
Böhm, M. "Alterations of β-adrenoceptor-G-protein-regulated Adenylyl Cyclase in Heart Failure" Molecular and Cellular Biochemistry 1995 147:147-160.
Bond et al. "Physiological Effects of Inverse Agonists in Transgenic Mice with Myocardial Overexpression of the $β_2$-adrenoceptor" Nature 1995 374:272-276.
Braunwald, E. "Pathophysiology of Heart Failure" Heart Disease 1988 14:426-448.
Bristow et al. "β-Adrenergic-Receptor Density" The New England Journal of Medicine 1982 307(4):205-211.
Bristow et al. "$β_1$- and $β_2$-Adrenergic-Receptor Subpopulations in Nonfailing and Failing Human Ventricular Myocardium: Coupling of Both Receptor Subtypes to Muscle Contraction and Selective $β_1$-Receptor Down-Regulation in Heart Failure" Circulation Research 1986 59:297-309.
Bristow et al. "Reduced $β_1$ Receptor Messenger RNA Abundance in the Failing Human Heart" The Journal of Clinical Investigation 1993 92:2737-2745.
Calderone et al. "Dysfunction of the β- and α-Adrenergic Systems in a Model of Congestive Heart Failure" Circulation Research 1991 69:332-343.
Chen et al. "Expression of Type V Adenylyl Cyclase Is Required for Epidermal Growth Factor-mediated Stimulation of cAMP Accumulation" The Journal of Biological Chemistry 1995 270(46):27525-27530.
Chern, Y. "Regulation of Adenylyl Cyclase in the Central Nervous System" Cellular Signalling 2000 12:195-204.
Côté et al. "Expression and Regulation of Adenylyl Cyclase Isoforms in the Human Adrenal Gland" The Journal of Clinical Endocrinology and Metabolism 2001 86(9):4495-4503.
Eschenhagen et al. "Veränderungen der Genexpression bei terminaler Myokardinsuffizienz" Zeitschrift für Kardiologie 1992 81(suppl. 4):33-40 Ab Abstract only.
Feldman et al. "Increase of the 40,000-mol wt Pertussis Toxin Substrate (G protein) in the Failing Human Heart" The Journal of Clinical Investigation 1988 82:189-197.
Fujita et al. "Alteration in Type V and VI Adenylyl Cyclase Isoform Gene Expression in Rat Heart with Monocrotaline-Induced Pulmonary Hypertension" Circulation 1994 90(No. 4 Part 2):I-584 Abstract 3146.
Gaudin et al. "Overexpression of $G_{Sα}$ Protein in the Hearts of Transgenic Mice" The Journal of Clinical Investigation 1995 95:1676-1683.
Glatt, C. E. and Snyder, S. H. "Cloning and Expression of an Adenylyl Cyclase Localized to the Corpus Striatum" Nature 1993 361: 536-538.
Hadcock et al. "Agonist-induced Destabilization of β-Adrenergic Receptor mRNA" The Journal of Biological Chemistry 1989 264(33):19928-19933.
Hadcock, J. R. and Malbon, C. C. "Down-Regulation of β-adrenergic Receptors: Agonist-induced Reduction in Receptor mRNA Levels" PNAS 1988 85:5021-5025.
Hammond et al. "Myocardial β-Adrenergic Receptor Expression and Signal Transduction after Chronic Volume-Overload Hypertrophy and Circulatory Congestion" Circulation 1992 85(1):269-280.
Holroyde et al. "The Calcium and Magnesium Binding Sites on Cardiac Troponin and their Role in the Regulation of Myofibrillar Adenosine Triphosphatase" The Journal of Biological Chemistry 1980 255(24):11688-11693.

(Continued)

Primary Examiner — Michael Szperka
Assistant Examiner — Marianne Dibrino
(74) Attorney, Agent, or Firm — Licata & Tyrell P.C.

(57) ABSTRACT

The invention relates to compositions and methods for diagnosing and treating cardiac conditions and neurodegenerative diseases using antibodies which specifically recognize and bind to the adenylyl cyclase 5 isoform in the heart and brain. These antibodies demonstrate high specificity to the AC5 isoform and do not cross react to any other AC5 isoform. The invention further relates to methods of delivery of drugs to the site of injured tissue using the antibodies of the present invention.

2 Claims, 16 Drawing Sheets

OTHER PUBLICATIONS

Ishikawa et al. "Downregulation of Adenylylcyclase Types V and VI mRNA Levels in Pacing-induced Heart Failure in Dogs" The Journal of Clinical Investigation 1994 93:2224-2229.

Ishikawa et al. "Isolation and Characterization of a Novel Cardiac Adenylylcyclase cDNA" The Journal of Biological Chemistry 1992 267(19):13553-13557.

Ishikawa, Y. *Advances in Second Messenger and Phosphoprotein Research*"Regulation of cAMP Signaling by Phosphorylation" Philadelphia, Pennsylvania: Lippincott-Raven 1998 p. 99-120.

Katsushika et al. "Cloning and Characterization of a Sixth Adenylyl Cyclase Isoform: Types V and VI Constitute a Subgroup within the Mammalian Adenylyl Cyclase Family" PNAS 1992 89:8774-8778.

Kim et al. "Functional Reconstitution of the Cardiac Sarcoplasmic Reticulum $Ca^{2+}$-ATPase with Phospholamban in Phospholipid Vesicles" The Journal of Biological Chemistry 1990 265(3):1702-1709.

Koch et al. "Cardiac Function in Mice Overexpressing the β-Adrenergic Receptor Kinase or a βARK Inhibitor" Science 1995 268:1350-1353.

Krebs, E. G. "The Phosphorylation of Proteins: a Major Mechanism for Biological Regulation" Biochemical Society Transactions 1985 13:813-820.

Krupinski et al. "Molecular Diversity in the Adenylylcyclase Family" The Journal of Biological Chemistry 1992 267(34):24858-24862.

Liang et al. "Decreased Adrenergic Neuronal Uptake Activity in Experimental Right Heart Failure" The Journal of Clinical Investigation 1989 84:1267-1275.

Liu et al. "Expression of Type VI Adenylyl Cyclase in the Central Nervous System: Implication for a Potential Regulator of Multiple Signals in Different Neurotransmitter Systems" FEBS Letters 1998 436:92-98.

Ludwig, M. and Seuwen, K. "Characterization of the Human Adenylyl Cyclase Gene Family: cDNA, Gene Structure, and Tissue Distribution of the Nine Isoforms" Journal of Receptors and Signal Transduction 2002 22(1-4):79-110.

Mahan et al. "Genetic Analysis of β-Adrenergic Receptor Internalization and Down-regulation" PNAS 1985 82:129-133.

Manolopoulos et al. "Adenylyl Cyclase Isoforms Are Differentially Expressed in Primary Cultures of Endothelial Cells and Whole Tissue Homogenates from Various Rat Tissues" Biochemical and Biophysical Research Communications 1995 208(1):323-331.

Marzo et al. "β-Adrenergic Receptor-G Protein-adenylate Cyclase Complex in Experimental Canine Congestive Heart Failure Produced by Rapid Ventricular Pacing" Circulation Research 1991 69:1546-1556.

Neumann et al. "Increase in Myocardial $G_i$-proteins in Heart Failure" The Lancet 1988 936-937.

Nishi et al. "Amplification of Dopaminergic Signaling by a Positive Feedback Loop" PNAS 2000 97(23):12840-12845.

Okumura et al. "Disruption of Type 5 Adenylyl Cyclase Gene Preserves Cardiac Function Against Pressure Overload" PNAS 2003 100(17):9986-9990.

Roth et al. "Downregulation of Cardiac Guanosine 5'—Triphosphate-binding Proteins in Right Atrium and Left Ventricle in Pacing-induced Congestive Heart Failure" The Journal of Clinical Investigation 1993 91:939-949.

Scott, J. D. "Cyclic Nucleotide-Dependent Protein Kinases" Pharmacology and Therapeutics 1991 50:123-145.

Soderling, S. H. and Beavo, J. A. "Regulation of cAMP and cGMP Signaling: New Phosphodiesterases and New Functions" Current Opinion in Cell Biology 2000 12:174-179.

Ungerer et al. "Altered Expression of β-Adrenergic Receptor Kinase and $β_1$-Adrenergic Receptors in the Failing Human Heart" Circulation 1993 87:454-463.

Urasawa, K. and Insel, P. A. *G-Proteins Signal Transduction and Disease* "GTP-Binding Proteins and Cardiovascular Disease" London, England: Academic Press Limited 1992 p. 47-85.

Wallach et al. "Molecular Cloning and Expression of a Novel Type V Adenylyl Cyclase from Rabbit Myocardium" FEBS Letters 1994 338:257-263.

Watson et al. "Molecular Cloning and Characterization of the Type VII Isoform of Mammalian Adenylyl Cyclase Expressed Widely in Mouse Tissues and in S49 Mouse Lymphoma Cells" The Journal of Biological Chemistry 1994 269(46):28893-28898.

Yamamoto et al. "β-Adrenoceptor-G Protein-Adenylate Cyclase Complex in Rat Hearts with Ischemic Heart Failure Produced by Coronary Artery Ligation" Journal of Molecular and Cellular Cardiology 1994 26:617-626.

Yoshimura, M. and Cooper, D. M. F. "Cloning and Expression of a $Ca^{2+}$-inhibitable Adenylyl Cyclase from NCB-20 Cells" PNAS 1992 89:6716-6720.

Yu et al. "Determination and Cellular Localization of Adenylyl Cyclase Isozymes Expressed in Embryonic Chick Heart" FEBS Letters 1995 374:89-94.

* cited by examiner

Fig. 1: Immunoblotting with 19D5.C1 (1:100)

M: Molecular weight marker
1: AC5 Wild type (mice brain)
2: AC5 Knock out (mice brain)
3: AC5 Over-expressed (mice brain)

Fig 2: Immunoblotting with Commercial ACV/VI (1:200)

M: Molecular weight marker
1: AC5 Wild type (mice brain)
2: AC5 Knock out (mice brain)
3: AC5 Over-expressed (mice brain)

The peptide ordered for Adenylyl Cyclase Type5(C1b portion)

Ac-GNQVSKEMKRMGFEDPKDKNC-amide.

Figure 3

Figure 4
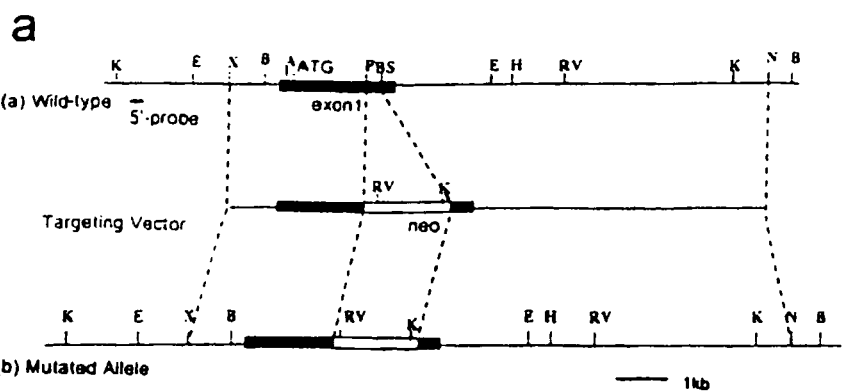
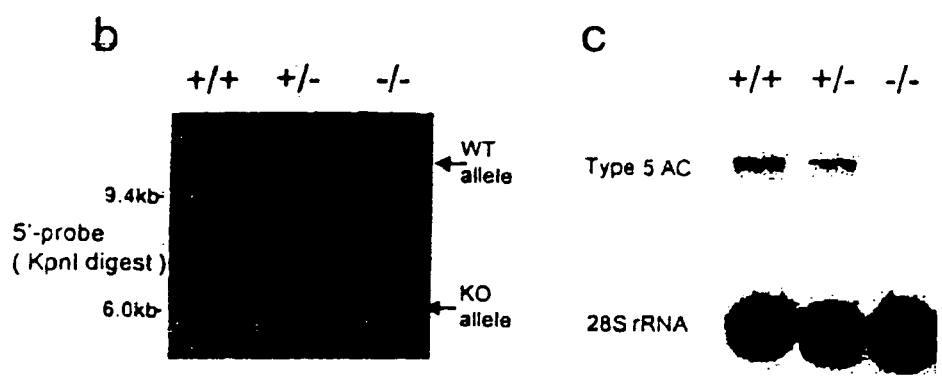
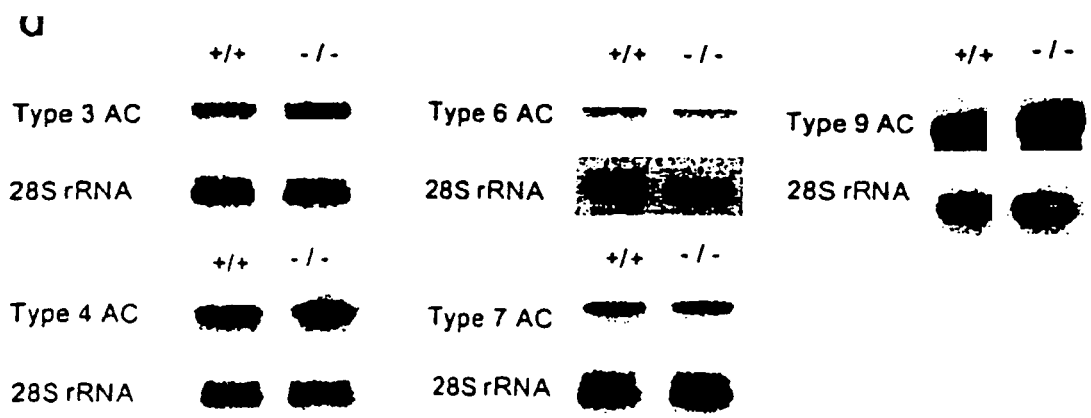

ADENYLYL CYCLASE ANTIBODIES, COMPOSITIONS AND USES THEREOF

GOVERNMENT SUPPORT

The invention described herein was supported in whole or in part by the National Institutes of Health, Grant Nos. 1 PO1HL69020; 1 PO1H159139; 5 RO1 AG14121 and 1 RO1 AG023137. The United States Government has certain rights in the invention.

FIELD OF THE INVENTION

The present invention relates generally to the fields of cardiology and neurology, and more particularly to the identification of antibodies that recognize and react with specific isoforms of adenylyl cyclase, an enzyme known to play a key regulatory role in cell function. The invention also relates to diagnostic and therapeutic materials and methods, including by way of example, pharmaceutical compositions, methods of treatment of diseases associated with neurological and/or cardiac impairment, and screening assays.

BACKGROUND OF THE INVENTION

Cyclic AMP is a major second messenger that converts an extracellular signal to an intracellular signal. The enzyme responsible for its formation is adenylyl cyclase (AC), which is a membrane bound enzyme that catalyzes the conversion of ATP to cyclic AMP (cAMP) upon stimulation of various Gs protein-coupled receptors by neurotransmitters and hormones. Cyclic AMP then activates protein kinase A (PKA) by dissociating its regulatory subunit from the catalytic subunit (Scott, J. D, (1991) Pharmac. Ther. 50:123-145). The catalytic subunit of PKA then initiates an enzymatic cascade of phosphorylation reactions within the cell, for example, various enzymes involved in myocyte contraction in the heart, such as troponin (Holroyde, M. J., Robertson, S. P., Johnson, J. D., Solaro, R. J., and Potter, J. D (1980), J. Biol. Chem. 255:11668-11693), phospholamban (Kim, H. W., Steenaart, N. A. E., Ferguson, D. G., and Kranias, E. G, (1990), J. Biol. Chem. 265:1702-1709), those involved in glucose metabolism in the liver, such as glycogen phosphorylase (Krebs, E. G. (1985), Biochem. Soc. Trans. 13:813-820), and those involved in neuronal function (Nishi, A., Bibb, J. A., Snyder, G. L., Higashi, H., Naim, A. C., and Greengard, P. (2000), Proc. Natl. Acad. Sci. U S A 97:12840-12845). By phosphorylating uniquely differentiated proteins in each cell type, cAMP signaling and thus PKA regulate the unique function of each organ. Cyclic AMP is eventually degraded to AMP by phosphodiesterase (Soderling, S. H., and Beavo, J. A. (2000) Curr Opin Cell Biol 12:174-179). PKA is inactivated by re-association of the catalytic subunit with the regulatory subunit (Ishikawa, Y. (1998), Regulation ofcAMP signaling by phosphorylation. In Adenylyl cyclases. D. M. F. Cooper, editor. Philadelphia: Lippincott-Raven Publishers. 99-120). Phosphorylated proteins are dephosphorylated by phosphatases, thereby pulling the protein conformation back into an inactive form.

Molecular cloning studies have elucidated the presence of at least 9 isoforms of adenylyl cyclase that differ in biochemical properties and tissue distribution. All AC isoforms share the same membrane topology, i.e., a tandem repetition of a six-transmembrane domain and a large cytoplasmic domain. The amino acid sequence within the membrane domain is not conserved among these isoforms; however, that of the cytoplasmic domain is relatively well-conserved and is considered to be the catalytic domain. Interestingly, a group of isoforms shows higher amino acid sequence homology with each other than with other isoforms. Subsequent biochemical studies also revealed that certain isoforms share not only a similar amino acid sequence, but also display similar biochemical properties. Based upon amino acid sequence homology, biochemical properties, and tissue distribution, the nine isoforms can be subdivided into at least five subgroups. Importantly, the diversity in their biochemical properties, in particular, regulation by calmodulin and G beta/gamma subunits, and in their tissue distribution may explain the conflicting findings of earlier studies in which membrane preparations from a variety of different tissues were used for AC assays. Furthermore, the finding of diversity in the AC isoforms and in their regulation during the past decade has expanded our understanding of this classic intracellular signaling pathway. One of the questions yet remaining is the specific role of each isoform in a given cell type and organ function. A particular AC isoform must play a specific role in regulating the physiological function of a given organ. Unfortunately, previous in vitro experimental approaches were unable to address this issue.

The distribution of the AC isoforms within the brain is heterogeneous, suggesting that each isoform is involved in a distinct aspect of neuronal signaling (Cooper, D., editor. (1998), Adenylyl cyclases. Philadelphia: Lippincott-Raven Publishers). The hippocampus is rich in AC1 and since this isoform is activated by Ca-calmodulin, it has been speculated that it plays a role in long-term potentiation mediated by the glutamate receptor. The olfactory bulb is rich in AC3. AC5 is most dominant in the striatum, implicating its involvement in motor regulation (Glatt, C. E., and Snyder, S. H. (1993) Nature 361:536-538). AC5 is located mostly in medium-sized striatal neuronal cells expressing D1 dopaminergic receptors in the basal ganglia, and accordingly has been implicated in signal detection to dopaminergic function. In contrast, most AC6 is present in most neurons and is co-localized with various neurotransmitters systems, AC6 might be in regulation of the classical neuronal signal integration on the brain (Liu, F. C., Wu, G. C., Hsieh, S. T., Lai, H. L., Wang, H. F., Wang, T. W., and Chem, Y. (1998), FEBS Lett 436:92-98). However, the role of these isoforms in neuronal function in vivo is poorly understood. A key question that remains unanswered is what the specific role of an AC isoform is in neuronal function and cAMP signal whose expression is limited to a specific brain region.

A number of neurotransmitters and neuromodulators in the brain are mediated though G protein-coupled receptors, including those of the classical neurotransmitters, dopamine, serotonin, and adrenaline. All the AC isoforms are subject to the regulation of G proteins and thus AC is a crucial molecule in modulating the physiological responses of this broadly expressed neurotransmission and neuromodulation system. The diversity of the AC family members may allow each isoform to function in a different signal transduction pathway of neurotransmitters, neuromodulators or neurotrophic factors. This is particularly important for the neuronal system, unlike the heart, in which a single neuron may receive stimulating and/or sequential multiple inputs from other neurons in a fraction of a second. Further, the mode of this input may differ from one region of the brain to another. The coincidence detector of AC renders neurons capable of detecting simultaneous stimulation of two or more neurotransmitters. This neuronal integration of multiple signals may be determined by the biochemical characteristics of the AC that is expressed by the particular neuron. Because of the complexity and extensive involvement of AC in neuronal information processing, AC has been implicated in biological functions from synaptic plasticity and circadian rhythms (Chern, Y. (2000), Cell Signal 12:195-204).

It is well known that cAMP plays a major role in regulating cardiac function. Adult cardiac myocytes express multiple AC isoforms, with AC-5 as the dominant AC isoform. However, both the physiological significance of the existence of multiple isoforms and the role of AC-5 in the regulation of cAMP signal, in particular relative to that of AC-6, in intact heart have been very poorly understood.

Congestive heart failure (CHF) represents one of the major public health problems in most Western countries, but its pathophysiology remains largely unknown. Improved therapy could be offered to patients with heart failure if its molecular and genetic mechanisms were better defined.

Congestive heart failure (CHF) is defined as abnormal heart function resulting in inadequate cardiac output for metabolic needs (Braunwald, E. led), In: Heart Disease, W.B. Saunders, Philadelphia, page 426, 1988). Symptoms include breathlessness, fatigue, weakness, leg swelling, and exercise intolerance. On physical examination, patients with heart failure tend to have elevations in heart and respiratory rates, rales (an indication of fluid in the lungs), edema, jugular venous distension, and, in general, enlarged hearts. The most common cause of CHF is atherosclerosis, which causes blockages in the blood vessels (coronary arteries) that provide blood flow to the heart muscle. Ultimately such blockages may cause myocardial infarction (death of heart muscle) with subsequent decline in heart function and resultant heart failure. Other causes of CHF include valvular heart disease, hypertension, viral infections of the heart, alcohol, and diabetes. Some cases of heart failure occur without clear etiology and are called idiopathic.

CHF is also typically accompanied by alterations in one or more aspects of beta-adrenergic neurohumoral function; see, e.g., Bristow M R, et al., N Engl J Med 307:205-211, (1982); Bristow M R, et al., Circ Res 59:297-309, (1986); Ungerer M, et al., Circulation 87: 454-461, (1993); Feldman A M, et al., J Clin Invest 82:189-197, (1988); Bristow M R, et al., J Clin Invest 92: 2737-2745, (1993); Calderone A, et al., Circ Res 69:332-343, (1991); Marzo K P, et al., Circ Res 69:1546-1556, (1991); Liang C-S, et al., J Clin Invest 84: 1267-1275, (1989); Roth D A, et al., J Clin Invest 91: 939-949, (1993); Hadcock J R and Malbon C C: Proc Natl Acad Sci 85:5021-5025, (1988); Hadcock J R, et al., J Biol Chem 264: 19928-19933, (1989); Mahan, et al., Proc Natl Acad Sci USA 82:129-133, (1985); Hammond H K, et al., Circulation 85:269-280, (1992); Neumann J, et al., Lancet 2: 936-937, (1988); Urasawa K, et al., In: G Proteins: Signal Transduction and Disease, Academic Press, London. 44-85, (1992); Bohm M, Mol Cell Biochem, 147: 147-160, (1995); Eschenhage T, et al., Z Kardiol, 81 (Suppl 4): 33-40, (1992); and Yamamoto J, et al., J Mol Cell, 26: 617-626, (1994). See also the numerous additional references regarding various adenylylcyclase enzymes by, e.g., Fujita M et al., Circulation, 90: (No. 4 Part 2), (1994); Yoshimura M et al., Proc Natl Acad Sci USA, 89:6716-6720, (1992); Krupinski J et al., J Biol Chem, 267: 24858-24862, (1992); Ishikawa Y et al., J Biol Chem, 267: 13553-13557, (1992); Ishikawa Y et al., J. Clin Invest, 93:2224-2229, (1994); Katsushika S et al., Proc Natl Acad Sci USA, 89:8774-8778, (1992); Wallach J et al., FEBS Lett, 338:257-263, (1994); Watson P A et al., J Biol Chem, 269: 28893-28898, (1994); Manolopoulos V G et al., Biochem Biophys Res Commun, 208:323-331, (1995); Yu H J et al., FEBS Lett, 374:89-94, (1995); and Chen Z et al., J Biol Chem, 270:27525-27530, (1995).

As a result of these studies and others, efforts to treat CHF have focused on the administration of pharmacological agents, such as catecholamines and other beta-adrenergic agonists, as means of stimulating beta-adrenergic responses in dysfunctional hearts. Such therapeutic approaches have been only partly successful. Furthermore, long-term exposure to catecholamines can be detrimental. In particular, the heart tends to become less responsive to beta-adrenergic stimulation, and such unresponsiveness is typically associated with high levels of catecholamines in plasma, a factor generally linked to a poor prognosis.

Present treatments for CHF include pharmacological therapies, coronary revascularization procedures (e.g. coronary artery bypass surgery and angioplasty), and heart transplantation. Pharmacological therapies have been directed toward increasing the force of contraction of the heart (by using inotropic agents such as digitalis and beta-adrenergic receptor agonists), reducing fluid accumulation in the lungs and elsewhere (by using diuretics), and reducing the work of the heart (by using agents that decrease systemic vascular resistance such as angiotensin converting enzyme inhibitors). Beta-adrenergic receptor antagonists have also been tested. While such pharmacological agents can improve symptoms, and potentially prolong life, the prognosis in most cases remains dismal.

Some patients with heart failure due to associated coronary artery disease can benefit, at least temporarily, by revascularization procedures such as coronary artery bypass surgery and angioplasty. Such procedures are of potential benefit when the heart muscle is not dead but may be dysfunctional because of inadequate blood flow. If normal coronary blood flow is restored, viable dysfunctional myocardium may contract more normally, and heart function may improve. However, revascularization rarely restores cardiac function to normal or near-normal levels in patients with CHF, even though mild improvements are sometimes noted.

Finally, heart transplantation can be a suitable option for patients who have no other confounding diseases and are relatively young, but this is an option for only a small number of patients with heart failure, and only at great expense. In summary, CHF has a very poor prognosis and responds poorly to current therapies.

Further complicating the physiological conditions associated with CHF, are various natural adaptations that tend to occur in patients with dysfunctional hearts. Although these natural responses can initially improve heart function, they ultimately result in problems that can exacerbate CHF, confound treatment, and have adverse effects on survival. There are three such adaptive responses commonly observed in CHF: (i) volume retention induced by changes in sodium reabsorption, which expands plasma volume and initially improves cardiac output; (ii) cardiac enlargement (from dilation and hypertrophy) which can increase stroke volume while maintaining relatively normal wall tension; and (iii) increased norepinephrine release from adrenergic nerve terminals impinging on the heart which, by interacting with cardiac .beta.-adrenergic receptors, tends to increase heart rate and force of contraction, thereby increasing cardiac output. However, each of these three natural adaptations tends ultimately to fail for various reasons. In particular, fluid retention tends to result in edema and retained fluid in the lungs that impairs breathing; heart enlargement can lead to deleterious left ventricular remodeling with subsequent severe dilation and increased wall tension, thus exacerbating CHF; and long-term exposure of the heart to norepinephrine tends to make the heart unresponsive to adrenergic stimulation and is linked with poor prognosis.

Controlled use of pharmacological agents, such as beta-adrenergic agonists; and other modulatory drugs, thus remains one of the major forms of treatment despite its shortfalls, including its potentially adverse effect on survival. Researchers who have analyzed and in some cases cloned DNA sequences encoding individual components involved in the beta-adrenergic receptor pathway have proposed using such components to identify new classes of drugs that might prove more useful in treating CHF. For example, Ishikawa et al. cloned DNA encoding two different isoforms of adenylyl cyclase ($AC_V$ and $AC_{VI}$) that are known to be predominant in mammalian cardiac tissue, and proposed using the DNA and/or recombinant protein to identify new classes of drugs that might stimulate adrenergic pathways (See, e.g., American Cyanamid, WO 93/05061, Mar. 18, 1993, and EP 0 529 662, Mar. 3, 1993; and Ishikawa U.S. Pat. No. 5,334,521, issued Aug. 2, 1994). In other reports in which cloned components of the adrenergic stimulation pathway were investigated, the authors generated transgenic mice overexpressing certain components (including cardiac β2-adrenergic receptors, $Gs_\alpha$ and G-protein receptor kinase inhibitors) and obtained some data suggesting that β-adrenergic stimulation may be enhanced in transgenic mice (see, e.g., Gaudin C, et al., J Clin Invest 95: 1676-1683, (1995); Koch W J, et al., Science 268: 1350-1353, (1995); and Bond R A, et al., Nature 364: 272-276, (1995)). None of these reports showed that cardiac function could be effectively restored in animals with heart failure, nor did they show that adrenergic responsiveness could be enhanced in large animal models that would be considered predictive of success in treating CHF in humans.

Indeed, reflecting on the observed difficulties associated with the clinical use of beta-adrenergic agonists (such as dopamine and dobutamine), a recent review concluded that beta-adrenergic stimulation appears to be harmful; and that, on the contrary, beta receptor "blockers" or antagonists may be more useful for improving morbidity and mortality rates (see, e.g., Baughman, K., Cardiology Clinics 13: 27-34, (1995)). While some agents may improve symptoms, the prognosis for patients receiving such pharmacological agents remains dismal.

As described herein, the expression of the type 5 AC isoform is limited to the heart and the striatum of the brain and is negligibly expressed in other tissues. The physiological significance of this cardiac and striatum-specific localization is unknown. To address this issue, and to help in identification of new therapeutic approaches for the treatment of cardiac and/or neurological impairment, the inventors of the present application have developed a transgenic mouse model lacking the expression of AC5. Furthermore, up until the time of the present invention, there was a lack of antibodies with the specificity needed to identify and quantify the type and amount of each isoform associated with a specific tissue. In particular, an AC5 monoclonal antibody with high specificity was not available up until the time of the present invention to distinctly identify and quantitate the presence of AC5 in specific tissue. The therapeutic and diagnostic utility of this AC5 specific monoclonal antibody is described herein.

The citation of any reference herein should not be construed as an admission that such reference is available as "Prior Art" to the instant application.

SUMMARY OF THE INVENTION

The present invention provides for compositions and methods for treating mammals suffering from cardiovascular and neurological diseases and conditions. In particular, methods and pharmaceutical compositions for enhancing cardiac and neuronal function in mammals through use of an antibody specific for adenylyl cyclase 5 are disclosed.

Accordingly, a first aspect of the invention provides for an antibody to adenylyl cyclase 5, which is characterized by its ability to specifically bind to adenyl cyclase 5, but does not bind to or cross react with adenylyl cyclase 6 or to any other adenylyl cyclase enzyme. In a preferred embodiment, the antibody is a monoclonal antibody capable of specifically binding to adenylyl cyclase 5 (AC5). In a more preferred embodiment, the monoclonal antibody is the 19D5.C1 antibody, which demonstrates high specificity for the AC5 isoform and is produced by the hybridoma having ATCC accession number PTA-5800.

A second aspect of the invention provides for the hybridoma having ATCC accession number PTA-5880, which produces a monoclonal antibody, 19D5.C1, which is capable of specifically binding adenylyl cyclase 5 (AC5) without cross reacting to adenylyl cyclase 6 or to any other adenylyl cyclase enzyme.

A third aspect of the invention provides for a method of treating a mammal suffering from a cardiac condition, comprising administering to said mammal a therapeutically effective amount of an antibody specific for AC5. In a preferred embodiment, the antibody is a monoclonal antibody 19D5.C1, produced by the hybridoma having ATCC accession number PTA-5880, and a pharmaceutically acceptable carrier. In another preferred embodiment, the mammal is a human. In another preferred embodiment, the cardiac condition is selected from the group consisting of congestive heart failure, cardiac hypertrophy, ischemic heart disease, myocardial infarction, angina, hypertension, arrhythmias, aging cardiomyopathy, and idiopathic cardiomyopathy.

In a further preferred embodiment, the antibody is administered enterally or parenterally. In a yet further preferred embodiment, the antibody is administered intravenously, intramuscularly, subcutaneously, sublingually, or bucally. In another preferred embodiment, the antibody is administered prior to, during or after a heart procedure selected from the group consisting of bypass surgery, thrombolysis, angioplasty and any surgical procedure which involves manipulation of the heart. Another embodiment provides for the use of an antibody that specifically binds to adenyl cyclase 5, but does not bind to or cross react with adenylyl cyclase 6 or to any other adenylyl cyclase enzyme, for treating a cardiac condition. Another embodiment provides for the use of the monoclonal antibody designated 19D5.C1 produced by the hybridoma having ATCC accession number PTA-5880 for treating a cardiac condition.

A fourth aspect of the invention provides for a method of inhibiting apoptosis in myocytes, wherein said method comprises treatment with an antibody specific for AC5 in vitro or in vivo. In a preferred embodiment, the antibody is selected from the group consisting of a human antibody, a mouse antibody, a rat antibody, a goat antibody, a sheep antibody, a rabbit antibody, and a horse antibody. The antibody may be a humanized or a chimeric antibody. In a more preferred embodiment, the mouse antibody is the monoclonal antibody 19D5.C1 produced by the hybridoma having ATCC accession number PTA-5880. Another embodiment provides for the use of an antibody that specifically binds to adenyl cyclase 5, but does not bind to or cross react with adenylyl cyclase 6 or to any other adenylyl cyclase enzyme, for inhibiting apoptosis in myocytes in vivo or in vitro. Another embodiment provides for the use of the monoclonal antibody designated 19D5.C1 produced by the hybridoma having ATCC accession number PTA-5880 for inhibiting apoptosis in myocytes in vivo or in vitro.

A fifth aspect of the invention provides for a method for screening, diagnosis or prognosis of a cardiac condition selected from the group consisting of congestive heart failure, cardiac hypertrophy, ischemic heart disease, myocardial infarction and angina, said method comprising:

(I) measuring an amount of the AC5 gene or gene product in a tissue sample derived from the subject, wherein said AC5 gene or gene product is:
  (a) a DNA encoding adenylyl cyclase 5, or a nucleic acid derived therefrom;
  (b) a protein comprising adenylyl cyclase 5;
  (c) a nucleic acid comprising a sequence hybridizable to adenylyl cyclase 5, or its complement under conditions of high stringency, or a protein comprising a sequence encoded by said hybridizable sequence;
  (d) a nucleic acid at least 90% homologous to adenylyl cyclase 5, or its complement as determined using the NBLAST algorithm; or a protein encoded thereby; and (II) comparing the amount of said adenylyl cyclase 5 gene product in the subject with the amount of adenylyl cyclase 5 gene product present in a normal, non-damaged cardiac tissue sample or predetermined standard for normal, non-damaged cardiac tissue sample, wherein an elevated amount of said adenylyl cyclase 5 gene product in the subject compared to the amount in the normal, non-damaged cardiac tissue sample or predetermined standard for a normal, non-damaged cardiac tissue sample indicates a risk of developing a cardiac condition in the subject.

In a preferred embodiment, the tissue sample is selected from the group consisting of biopsied cardiac tissue, whole blood, plasma and serum. In another preferred embodiment, the method is used for monitoring the effect of therapy administered to a subject having a cardiac condition.

A sixth aspect of the invention provides for delivery or targeting of drugs for improvement of neurological function to patients in need of such therapy comprising conjugation of the drugs to an antibody specific for AC5 for delivery to the site where administration of the drug produces the desired effect. In a preferred embodiment, the antibody is selected from the group consisting of a human antibody, a mouse antibody, a rat antibody, a goat antibody, a sheep antibody, a rabbit antibody, and a horse antibody. The antibody may be a humanized or a chimeric antibody. In a more preferred embodiment, the mouse antibody is the monoclonal antibody 19D5.C1 produced by the hybridoma having ATCC accession number PTA-5880. In another preferred embodiment, the improvement in neurological function comprises an improvement in motor function. In another preferred embodiment, the patient in need of such improvement is a human patient. In another preferred embodiment, the neurological conditions to be treated may be selected from the group consisting of Parkinson's disease, amyotrophic lateral sclerosis (ALS), stroke, Alzheimer's disease and any other neurological disease or condition wherein the affected cells or tissues express the adenylyl cyclase 5 enzyme. In another preferred embodiment, drugs that act as dopamine agonists may be conjugated to the AC5 antibody for treatment of Parkinson's disease. In a particular embodiment, the drug may be a selective dopamine receptor agonist or a forskolin like agonist. Another embodiment provides for the use of an antibody that specifically binds to adenyl cyclase 5, but does not bind to or cross react with adenylyl cyclase 6 or to any other adenylyl cyclase enzyme, for delivery or targeting of drugs for improvement of neurological function to patients in need of such therapy. Another embodiment provides for the use of the monoclonal antibody designated 19D5.C1 produced by the hybridoma having ATCC accession number PTA-5880 for delivery or targeting of drugs for improvement of neurological function to patients in need of such therapy.

A seventh aspect of the invention provides for a pharmaceutical composition comprising a therapeutically effective amount of an antibody that binds to, or reacts specifically with AC5, and a pharmaceutically acceptable carrier. In a preferred embodiment, the antibody is a monoclonal antibody 19D5.C1 that is produced by the hybridoma having accession number PTA-5880. In another preferred embodiment, the pharmaceutical composition comprises a therapeutically effective amount of a drug for treating either cardiovascular disease or a neurological disease and an antibody specific for AC5 and a pharmaceutically acceptable carrier. In a situation whereby the pharmaceutical composition will be used to treat a neurological disease or condition, the drug may be coupled by chemical or other means to the antibody specific for AC5 such that targeted therapy to the site of neurological injury is possible. In a situation whereby the pharmaceutical composition will be used to treat a cardiovascular disease, the pharmaceutical composition is envisioned to be combination therapy wherein the AC5 antibody may be considered as adjunct therapy with the cardiovascular drug that is effective for treating such diseases. The cardiovascular drug plus the AC5 antibody together may exhibit an additive or a synergistic effect.

Accordingly, an eighth aspect of the invention provides for combination therapy using an antibody specific for AC5 in concert with an agent effective in treatment of a cardiac condition. In a preferred embodiment, the agent used in conjunction with AC5 for treatment of a cardiac condition may be selected from the group consisting of vasodilators, angiotensin II receptor antagonists, angiotensin converting enzyme inhibitors, diuretics, antithrombolytic agents, $\alpha$. or $\beta$-adrenergic receptor antagonists, $\alpha$.-adrenergic receptor antagonists, calcium channel blockers, and the like, which are available for treating cardiovascular and related diseases.

Other advantages of the present invention will become apparent from the ensuing detailed description taken in conjunction with the following illustrative drawings.

BRIEF DESCRIPTION OF THE DRAWINGS

FIG. 3 The sequence SEQ ID NO:1 from the C1b portion of AC5 used to immunize mice from which the 19D5.C1 monoclonal antibody was derived.

FIG. 4a): Targeted disruption of the AC5 gene in a non-conditional manner: (a) Partial structure of the AC5 gene (Wild type), targeting vector construct (Targeting vector), and (b) resultant mutated allele are shown. The position of the pgk-neo cassette (neo) and 5'-probe(EcoRI-HindIII; 400-bp) are indicated. K, KpnI; E, EcoRI; X, XhoI, A, ApaI; P, PstI; BS, BssHII, S, SpeI, H, HindIII, RV, EcoR V; N, NcoI; B, BamHI.

FIG. 4b): Southern blot analysis of genomic DNA from the offspring of F1-heterozygote intercross using 5'-probe.

FIG. 4c): Comparison of mRNA expression in AC5 and non-disrupted wild type ("WT") mouse.

FIG. 4d): RNase protection assay showing no compensatory increase in AC3, AC4, AC6, AC7, or AC9 upon disruption of AC5 gene in mice FIG. 5a): Comparison of steady state AC activity measured as maximal capacity of cAMP production in heart membranes of AC5KO and WT in the presence of ISO (100 μM ISO+100 μM GTP), GTPγS (100 μM) or forskolin (100 μM).

DETAILED DESCRIPTION OF THE INVENTION

Figure 1:
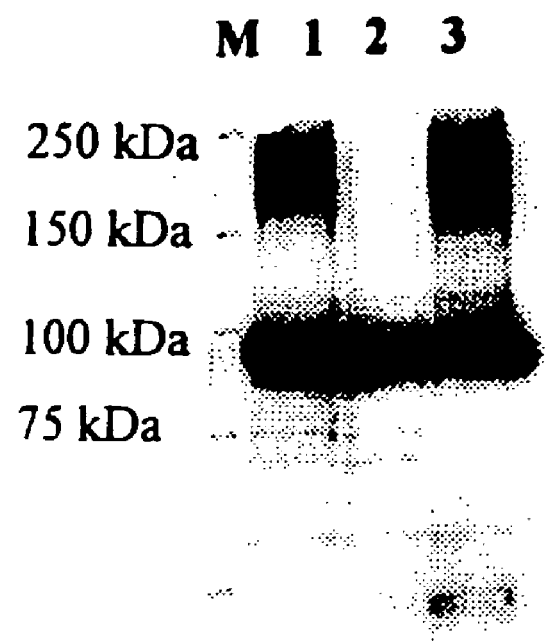
FIG. 1 Western Blot analysis using the 19D5.C1 monoclonal antibody with brain tissue derived from 1) AC5 wild type mice; 2) AC5 knock out mice; and 3) AC5 over-expressed mice.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference in their entireties.

Definitions

As noted above, the terms used herein have the meanings recognized and known to those of skill in the art. However, for convenience and completeness, particular terms and their meanings are set forth below.

"Adenylylcyclase" (also known as "adenylcyclase", "adenylate cyclase", and "cAMP synthetase") is an enzyme that catalyzes the conversion of adenosine triphosphate (ATP) to 3':5'-cyclic adenosine monophosphate (cAMP). Adenylylcyclase (abbreviated herein as "AC") is known to exist in a number of different isoforms that are found in varying levels in most all mammalian tissues. The adenylylcyclases of the present invention are isoforms found to be predominant in mammalian heart tissue, particularly in cardiac myocytes; and in the striatum of the brain, as described in more detail below. In particular, the invention relates to antibodies specific for adenylyl cyclase 5, hereinafter referred to as "AC5".

The term "antibody" as used herein includes intact molecules as well as fragments thereof, such as Fab and F(ab')$_2$, which are capable of binding the epitopic determinant. Antibodies that bind the genes or gene products of the present invention can be prepared using intact polynucleotides or polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g., a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816, 397.). The antibody may be a single chain antibody. The antibody may be a human or a humanized antibody. The antibody may be prepared in mice, rats, goats, sheep, swine, dogs, cats, or horses.

"Artery" refers to a blood vessel through which blood passes away from the heart. Coronary arteries supply the tissues of the heart itself, while other arteries supply the remaining-organs of the body. The general structure of an artery consists of a lumen surrounded by a multi-layered arterial wall.

"Dopamine 1" refers to the Dopamine receptor responsible for aspects of motor function and cardiovascular function and increases cAMP.

"Dopamine 2" refers to the Dopamine receptor responsible for aspects of motor function and cardiovascular function and decreases cAMP.

"Dyskinesia" refers to abnormal involuntary movement.

"Dystonia" refers to a disabling but rarely fatal disorder characterized by involuntary muscle contractions which force certain parts of the body into abnormal, sometimes painful, movement or postures.

"Essential Tremor" refers to a neurological disorder involving shaking that is typically elicited with activity and purposeful movement. Tremors may be occasional, temporary or intermittent and may affect any part of the body.

"Gene Product" as used herein, unless otherwise indicated, is a protein or polypeptide encoded by specific nucleic acid sequences, and as used herein refers particularly to the adenylyl cyclase (AC) proteins which are the subject of the present application. In addition, a gene product may refer to a nucleic acid comprising a sequence hybridizable to the nucleic acid encoding AC or its complement under conditions of high stringency, or a protein comprising a sequence encoded by said hybridizable sequence; or a nucleic acid at least 90% homologous to the nucleic acid encoding AC or its complement as determined using the NBLAST algorithm; or a nucleic acid at least 90% homologous to the nucleic acid encoding AC or a fragment or derivative of any of the foregoing proteins or nucleic acids.

"Myoclonus" refers to a rapid spasm of the soft palate, facial muscles and the diagram, palatal myoclonus of the legs, nocturnal myoclonus. Palatal myoclonus is usually caused by lesions on the brain/nerve pathways whereas some nocturnal myoclonus may be caused by peripheral nerve disease and other cases are caused by unknown factors. Noncturnal myoclonus is also known as Restless Leg Syndrome.

"Hypertension" refers to a condition wherein the systolic pressure is consistently over 140 mm Hg, or the diastolic blood pressure is consistently over 90 mm Hg and may be caused by a variety of factors including water volume in the body, salt content of the body, condition of the kidneys, nervous system or blood vessels and hormone levels in the body. The condition of hypertension may also be induced by pharmacological compounds including but not limited to: corticosteroids and other hormones, including estrogens and birth control pills, cyclosporine, and nasal decongestants.

"Inhibitor" includes but is not limited to, any suitable molecule, compound, protein, antibody or fragment thereof, nucleic acid, formulation or substance that can regulate AC5 activity in such a way that AC5 activity is decreased. The inhibitor can include, but is not limited to, the antibody described herein, which exhibits specificity for AC5.

"Mammal" refers to any animal classified as a mammal, including humans, domestic and farm animals, and zoo, sports, and pet companion animals, and other domesticated animal such as, but not limited to, cattle, sheep, ferrets, swine, horses, poultry, rabbits, goats, dogs, cats, and the like. Preferred companion animals are dogs and cats. Preferably, the mammal is human.

"Motor Function" refers to the ability of a mammal to control both voluntary and involuntary movement.

"Neurodegenerative Disorders" refers to a broad class of disorders of the nervous system that present as neurodysfunction, especially the impairment of motor function, including but not limited to: Cerebral Palsy, Atrophy, Cerebrovascular ferrocalcinosis, motor neuron disease, peroneal muscular atrophy, Parkinson's disease, amyotrophic lateral sclerosis, and multiple sclerosis.

"Parenteral" refers to introduction of the therapeutic agent by any route other than the digestive system, including intravenous, intraarterial, intraperitoneal, intramuscular, intraventricular, intracranial, subcutaneous, subdermal, transvaginal, nasal or rectal routes.

"Enteral" as used in the present invention, refers to introduction of the therapeutic agent by way of delivery to the digestive system, eg. via oral delivery, or through a feeding tube such as a nasogastric tube.

"Mucosal" refers to the tissues in the body that secrete mucous; thus encompassing the oral cavity (nose, throat, and mouth), the digestive tract (including the intestines), as well as the rectum and vagina.

"Transmucosal" refers to the passage of materials across or through the mucosal membranes.

"Sublingual" refers to the area under the tongue.

"Sublingual delivery" refers to the systemic delivery of drugs or other agents through the mucosal membranes lining the floor of the mouth.

"Buccal" refers to the cheek area in the mouth.

"Buccal delivery" refers to administration of drugs or other agents through the mucosal membranes lining the cheeks (buccal mucosa).

"Subject" or "patient" refers to a mammal, preferably a human, in need of treatment for a condition, disorder or disease.

"Striatum" refers to part of the basal ganglia of the brain and is responsible for motor function.

"Stimulator" includes but is not limited to, any suitable molecule, compound, protein or fragment thereof, nucleic acid, formulation or substance that can regulate AC5 activity in such a way that AC5 activity is increased. The stimulator can include, but is not limited to, forskolin and its derivatives, divalent cations, peptides and enzymes.

"Therapeutically Effective Dose" refers to the dose that produces the effects for which it is administered.

"Treat" or "treatment" refers to both therapeutic treatment and prophylactic or preventative measures, wherein the object is to prevent or slow down (lessen) an undesired physiological condition, disorder or disease or to obtain beneficial or desired clinical results. For purposes of this invention, beneficial or desired clinical results include, but are not limited to, alleviation of symptoms; diminishment of extent of condition, disorder or disease; stabilization (i.e. not worsening) a state or condition, disorder or disease; delay or slowing of a condition, disorder, or disease progression; amelioration of the condition, disorder or disease state; remission (whether partial or total), whether detectable or undetectable; or enhancement or improvement of a condition, disorder or disease. Treatment includes eliciting a cellular response that is clinically significant, without excessive side effects. Treatment also includes prolonging survival as compared to expected survival without treatment A "therapeutically effective amount" is an amount sufficient to decrease or prevent the symptoms associated with the cardiac, neurological or other related conditions contemplated for therapy with the compositions of the present invention.

"Modulate" as used herein, refers to a compound or agent (including but not limited to proteins, polypeptides or fragments thereof, nucleotides, nucleic acid fragments, synthetic organic compounds, antibodies or fragments thereof) which are capable of increasing or decreasing the level and/or activity of a gene or gene product identified by the methods described herein. The genes or gene products may have a beneficial effect in amelioration of symptoms in certain diseases or conditions such as neurodegenerative diseases. On the other hand, in certain diseases or conditions, in particular those associated with cardiac dysfunction, it may be beneficial to downregulate the gene or gene product. These may include congestive heart failure, cardiac hypertrophy, angina, atherosclerosis or restenotic lesions, to name a few non-limiting examples. Those skilled in the art, based on the present description, will understand that such modulation can be determined by assays and techniques known to those of skill in the art, including as described in more detail herein.

"Agonist" as used herein, refers to a compound or agent (including but not limited to proteins, polypeptides, or fragments thereof, nucleotides, nucleic acid fragments, synthetic organic compounds, antibodies or fragments thereof) capable of increasing the level and/or activity of an AC5 molecule or a variant thereof and may be referred to herein as an agonist.

"Apoptosis" refers to "programmed cell death" and is characterized by certain cellular characteristics such as condensation of the chromatin and by a positive "TUNEL" staining pattern, or other standard assays known to those skilled in the art.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Chronic Pressure Overload" refers to a condition whereby there is an extra load placed on the heart, which may be due to one of many factors, including, but not limited to, constriction of the aorta, central hypertension, aortic stenosis, or by taking drugs that increase blood pressure. This extra load on the heart muscle may ultimately result in heart failure.

"Enhancing cardiac function" as used herein refers to increasing the ability of the heart to function at maximum capacity in terms of contractile function, stroke volume, increased LV ejection fraction and dP/dt.

"Enhancing Neurological Function" as used herein generally refers to an improvement in motor skills, although improvement in other neurological parameters may be encompassed by the aspects of the invention. For example, as related to stroke, speech and mentation may also be affected. Thus, an improvement in these neurological parameters is also encompassed by the aspects of the present invention.

The term "arrhythmia" refers to any change from the normal sequence of electrical impulses, causing abnormal heart rhythms. This can cause the heart to pump less effectively. Some arrhythmias are so brief (for example, a temporary pause or premature beat) that the overall heart rate or rhythm isn't greatly affected. But if arrhythmias last for some time, they may cause the heart rate to be too slow or too fast or the heart rhythm to be erratic. The term tachycardia refers to a heart rate of more than 100 beats per minute. Bradycardia describes a rate of less than 60 beats per minute.

"Cardiomyopathies" (CMPs) are primary heart muscle diseases clinically associated with heart failure and an increased risk of sudden cardiac death. Cardiomyopathy has many causes, including nutritional deficiencies, deposits in the heart muscle associated with medical conditions, anemia, stress, viral infections (rare), alcoholism, coronary artery disease, and others. In "idiopathic cardiomyopathy", there is no identifiable cause, although it is suspected to be an end stage of myocarditis. It can affect all ages and both sexes, but is most common in adult men.

"Cardiac hypertrophy" refers to a thickening of the muscle of the heart, in particular, an increased thickness of the wall of the cardiac chambers. It can involve the left ventricle or the right ventricle or both. It results from increased work of the chambers of the heart. This is usually associated with obstructions in the valves or blood vessels through which the ventricle must push the blood, or with high blood pressure.

"Coronary artery disease", also referred to as "ischemic heart disease" is a condition in which fatty deposits (atheroma) accumulate in the cells lining the wall of the coronary arteries. These fatty deposits build up gradually and irregularly in the large branches of the two main coronary arteries which encircle the heart and are the main source of its blood supply. This process is called atherosclerosis which leads to narrowing or hardening of the blood vessels supplying blood to the heart muscle (the coronary arteries). This results in ischemia (inability to provide adequate oxygen) to heart muscle and this can cause damage to the heart muscle. Complete occlusion of the blood vessel leads to a heart attack (myocardial infarction).

Angina pectoris, or "angina" is the medical term for chest pain or discomfort due to coronary heart disease. Angina is a symptom of a condition called myocardial ischemia. It occurs when the heart muscle (myocardium) doesn't get as much blood (hence as much oxygen) as it needs. This usually happens because one or more of the heart's arteries (blood vessels that supply blood to the heart muscle) is narrowed or blocked. Insufficient blood supply is called ischemia. Typical angina is uncomfortable pressure, fullness, squeezing or pain in the center of the chest. The discomfort also may be felt in the neck, jaw, shoulder, back or arm. Many types of chest discomfort aren't related to angina. Acid reflux (heartburn) and lung infection or inflammation are examples.

"Forskolin", like digitalis, is a natural plant extract, which has been used in traditional medicine. Forskolin, which is a classical pharmacological regulator which regulates the AC isoforms nonspecifically and increases the concentration of intracellular cAMP, can be used to develop an AC5 isoform specific regulator. Forskolin binds to the catalytic core at the opposite end of the same ventral cleft that contains the active site of the AC enzyme, and activates the enzyme by gluing together the two cytoplasmic domains in the core ($C_1$ and $C_2$) using a combination of hydrophobic and hydrogen bond interactions. As predicted by a recent crystallographic study, there is a relatively large open space between the C6/C7 positions of forskolin and its binding site within AC. It had been hypothesized, and subsequently demonstrated, that a forskolin derivative modified in these positions has altered isoform-selectivity without disruption of their activity. One example of such a derivative, which is a selective stimulator of AC5, is 6-[3-(dimethylamino)propionyl]-14,15 dihydro-forskolin (NKH477), a novel water-soluble forskolin derivative. Included within the scope of the derivatives of forskolin, forskolin-like molecules (molecules having similar activity as forskolin but with chemical modifications) and dopamine agonists are prodrugs of these molecules. In general, such prodrugs will be functional derivatives of such compounds which are readily convertible in vivo into the compound from which it is derived. Conventional procedures for the selection and preparation of suitable prodrug derivatives are described, for example, in "Design of Prodrugs" ed. H. Bundgaard, Elsevier, 1985. For the purposes of this application, a "forskolin-like molecule" is a forskolin derivative.

The term "derivative" or "derivatized" as used herein includes chemical modification of an agent, such as the chemical compounds or agents described herein, including but not limited to the forskolin or forskolin-like molecules or dopamine receptor agonists. Illustrative of such chemical modifications would be replacement of hydrogen by a halo group, an alkyl group, an acyl group or an amino group.

By way of example and not limitation, procedures using such conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10⁶ cpm $^{32}$P-labeled probe is used. Filters are incubated in hybridization mixture for 18-20 h at 40° C., and then washed for 1.5 h at 55° C in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency that may be used are well known in the art (e.g., as employed for cross-species hybridizations).

Procedures using such conditions of moderate stringency are as follows: filters comprising immobilized DNA are pretreated for 6 hours at 55° C. in a solution containing 6×SSC, 5×Denhardt's solution, 0.5% SDS and 100 µg/ml denatured salmon sperm DNA. Hybridizations are carried out in the same solution with 5–20×10⁶ cpm $^{32}$P-labeled probe. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well known in the art. (see, e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc.).

Procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency that may be used are well known in the art.

By "homologous" is meant a same sense nucleic acid which possesses a level of similarity with the target nucleic acid within reason and within standards known and accepted in the art. With regard to PCR, the term "homologous" may be used to refer to an amplicon that exhibits a high level of nucleic acid similarity to another nucleic acid, e.g., the template cDNA. As is understood in the art, enzymatic transcription has measurable and well known error rates (depending on the specific enzyme used), thus within the limits of transcriptional accuracy using the modes described herein, in that a skilled practitioner would understand that fidelity of enzymatic complementary strand synthesis is not absolute and that the amplified nucleic acid (i.e., amplicon) need not be completely identical in every nucleotide to the template nucleic acid.

"Complementary" is understood in its recognized meaning as identifying a nucleotide in one sequence that hybridizes (anneals) to a nucleotide in another sequence according to the rule A→T, U and C→G (and vice versa) and thus "matches" its partner for purposes of this definition. Enzymatic transcription has measurable and well known error rates (depending on the specific enzyme used), thus within the limits of transcriptional accuracy using the modes described herein, in that a skilled practitioner would understand that fidelity of enzymatic complementary strand synthesis is not absolute and that the amplicon need not be completely matched in every nucleotide to the target or template RNA.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleofide" and "oligonucleotide", and these terms will be used interchangeably. These terms refer only to the primary structure of the molecule. Thus, these terms include double- and single-stranded DNA, as well as double- and single-stranded RNA.

General Description

The enzyme adenylyl cyclase (AC), in particular the AC5 isoform, has been identified as the major AC isoform present in both cardiac and brain tissue. As shown by Applicants herein, this particular isoform, when present in heart tissue, can have a deleterious effect on cardiac function. On the other hand, the AC5 isoform, when expressed in brain tissue, serves a positive function in terms of enhanced production of cAMP and control of motor function.

Accordingly, the present invention relates to the discovery that elimination of the adenylyl cyclase 5 isoform or the nucleic acid encoding this isoform results in improvement in cardiac function following chronic pressure overload. Thus, as shown by Applicants herein, it would be advantageous to develop a means of inhibiting the expression of this gene or alternatively blocking the function of this gene or gene product through use of specific inhibitors. These inhibitors may be effective in the treatment of cardiac conditions and diseases characterized by elevated levels of AC5.

In particular, the invention relates to the identification of AC5 specific antibodies for inhibiting the expression and/or function of the AC5 gene and/or gene products and the use of these antibodies for enhancement of cardiac function. In a preferred embodiment, the invention provides for a monoclonal antibody specific for AC5, designated 19D5.C1, produced by a hybridoma having ATCC accession number PTA-5880. Another preferred embodiment provides for methods of using the AC5 monoclonal antibody or nucleic acids that encode said antibody for the treatment, prevention and diagnosis of cardiovascular disease. In a further preferred embodiment, the monoclonal antibody may be used to block or inhibit the expression and/or function of AC5 in order to enhance cardiac function.

Furthermore, in neurological diseases whereby the presence of high levels of AC5 is desirable, it would be advantageous to search for stimulators or agonists of the AC5 gene or gene product. Alternatively, the antibodies may be used to target stimulators of AC5 activity to the cells or tissues of the nervous system whereby such stimulators or agonists of AC5 activity would provide the desired effect.

Alternatively, while the antibodies described herein act to inhibit AC5 activity, and accordingly can be used as a line of independent therapy to treat cardiac conditions, it would also be advantageous to utilize the antibodies described herein for specific targeting of therapeutically effective drugs to the cardiovascular or nervous system to aid in treatment of specific cardiac conditions, including congestive heart failure, cardiac hypertrophy, ischemic heart disease, myocardial infarction, angina, hypertension, arrhythmias, aging cardiomyopathy, and idiopathic cardiomyopathy and agonists of said gene or gene products (AC5 and variants thereof, cDNA, RNA, and/or protein, small synthetic organic molecules) as targets for diagnosis, drug screening and therapies for cardiovascular diseases. Furthermore, the antibodies may be used as adjunct therapy with other known cardioprotective drugs as described below.

The present invention further relates to methods for the diagnostic evaluation and prognosis of cardiovascular disease in a subject animal. Preferably the subject is a mammal, more preferably the subject is a human. In a preferred embodiment the invention relates to methods for diagnostic evaluation and prognosis of cardiovascular disease using the antibodies of the present invention, preferably the AC5 monoclonal antibody designated as 19D5.C1. In particular, the antibodies may be used for detection of abnormal expression of the AC5 gene.

Antibodies or other binding partners to AC5 and variants thereof can be used in a diagnostic test to detect the presence of the AC5 gene or gene product in cells or in tissue biopsy.

The antibodies of the present invention can be used in the treatment of heart disease, especially congestive heart failure, cardiac hypertrophy, ischemic heart disease, myocardial infarction, and hypertension, angina, arrhythmias, aging cardiomyopathy, and idiopathic cardiomyopathy by blocking the expression and/or function of AC5. Methods of screening for novel compounds useful in treating cardiovascular and neurodegenerative diseases are also disclosed as are methods for delivery of drugs for treatment of cardiovascular and neurodegenerative diseases.

The present invention further relates to the generation of monoclonal antibodies specific for adenylyl cyclase 5, an isoform of adenylyl cyclase found in the heart and striatum in the brain.

Specifically, the present invention relates to methods of treating cardiac conditions using a monoclonal antibody obtained from a mammal-immunized with a peptide from the C1b region of adenylyl cyclase 5. This monoclonal (mAb) is referred to herein as 19D5.C1, and the hybridoma producing this monoclonal antibody was deposited Mar. 23, 2004 under the terms of the Budapest Treaty, with the American Type Culture Collection (ATCC) at 10801 University Blvd, Manassas VA 20110-2209, USA and given ATCC Accession No. PTA-5880. The sequence of the peptide used to generate the monoclonal antibody 19D5.C1 is shown in FIG. 3 and is designated as SEQ ID NO: 1.

The examples described in the present application demonstrate preferred embodiments of the invention. For the purpose of carrying out the experiments described below aimed at examining the specific role of type 5 AC in regulating cardiac and striatum-mediated motor function, a mouse line was developed in which the type 5 AC gene was disrupted. With regard to cardiac function, the specific questions addressed were whether elimination of type 5 AC (a) decreases either baseline cardiac function or HR, (b) impairs sympathetic stimulation or (c) alters parasympathetic modulation of cardiac function and HR. These questions were addressed using a combination of in vitro and in vivo approaches, e.g., by measuring cardiac function echocardiographically and HR in conscious mice, and assessing AC activity in vitro in cardiac membranes. Specifically, the effect of β-AR stimulation with ISO and muscarinic stimulation with acetylcholine (Ach), both under baseline conditions and also superimposed on β-AR stimulation was also examined. Parasympathetic neural function using intravenously (i.v.) administered phenylephrine to elicit baroreflex mediated slowing of HR, which is known to be predominantly a parasympathetic function were also examined. Further studies are described herein to determine the role of AC5 in neurological function using specific animal models to address this issue. The protocol for the AC5KO mouse model and the results obtained in these studies will follow in the Examples described herein.

Animal Models

As demonstrated herein, transgenic animals lacking the AC5 gene (AC5−/−) exhibit an increase in basal heart rate and baroflex-mediated bradycardia which suggests a loss of parasympathetic restraint and reduced $Ca^{2+}$ regulation of AC. In addition, using this AC5 knockout model, it was determined that the development of cardiac dysfunction following chronic pressure overload was decreased significantly compared to wild type mice, most likely due to a decrease in apoptosis in the AC5 knockout mice. Furthermore, it was determined that Bcl-2 protein, an inhibitor of apoptosis, was induced in response to pressure overload to a greater degree in the AC5 knockout mice as compared to wild type mice, which could be responsible for the protection against apoptosis. Accordingly, these experiments suggested that blocking the expression of the AC5 gene may be an effective strategy for treatment of cardiac conditions. Furthermore, the availability of this AC5−/− mouse model in conjunction with the use of its wild type counterpart, now provides a means to compare the effect of inhibitors of AC5 on cardiac function and determination of their potential for prevention of heart failure. The antibodies described herein, in particular, the 19D5.C1 monoclonal antibody, can be used to inhibit the expression and function of the AC5 gene and gene product, and may serve as a novel therapy for treatment of cardiac dysfunction.

Therapeutic Uses of the Invention

The invention described and claimed herein addresses and provides for novel antibodies and methods by which cardiac function can be effectively enhanced. Furthermore, the novel antibodies of the present invention may also be used for specific targeting of drugs to the nervous system to the site of injury or need.

Treatment of Cardiac Conditions

As described and illustrated in the studies described herein using the AC5 knockout mouse, it would be advantageous to block the expression or function of the AC5 gene or gene product to enhance cardiac function. This may be achieved through use of AC5 antagonists of either a chemical nature or a protein nature. Applicants have provided herein an antibody which exhibits a high degree of specificity for the AC5 isoform of the enzyme which may function to block expression or function of the enzyme, thus affording a novel therapeutic means for treatment of cardiac conditions. Accordingly, the methods of the present invention are likely to provide effective alternatives to present treatments for congestive heart failure and other cardiac conditions, including treating cardiovascular and related diseases, for example, hypertension, hypertrophy, arrhythmia, congestive heart failure, myocardial ischemia, angina, heart failure subsequent to myocardial infarction, myocardial infarction, ischemia reperfusion injury, aging cardiomyopathy, and idiopathic cardiomyopathy. For such a method, an AC5 specific antibody can be administered alone or concurrently with a known therapeutic cardiovascular agent, for example, angiotensin converting enzyme inhibitor, an angiotensin II receptor antagonist, a vasodilator, a diuretic, an α-adrenergic receptor antagonist, a β-adrenergic receptor antagonist, an antioxidant, or a mixture thereof.

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure can ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic and/or diastolic blood pressures. Hypertension places increased tension on the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ affected is the heart, this condition is known as myocardial ischemia, and myocardial ischemia initially leads to abnormal electrical activity. This can generate an arrhythmia. When myocardial ischemia is of sufficient severity and duration, cell injury can progress to cell death—i.e., myocardial infarction—and subsequently to heart failure, hypertrophy, or congestive heart failure.

When blood flow resumes to an organ after temporary cessation, this is known as ischemic reperfusion of the organ. For example, reperfusion of an ischemic myocardium can counter the effects of coronary occlusion, a condition that leads to myocardial ischemia. Ischemic reperfusion to the myocardium can lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Drug therapies, using known active ingredients such as vasodilators, angiotensin II receptor antagonists, angiotensin converting enzyme inhibitors, diuretics, antithrombolytic agents, α. or β-adrenergic receptor antagonists, α.-adrenergic receptor antagonists, calcium channel blockers, and the like, are available for treating cardiovascular and related diseases.

Moreover, the antibodies of the present invention, in particular 19D5.C1 can be administered concurrently with compounds that are already known to be suitable for treating the above-identified diseases. For example, methods of the invention include concurrently administering at least one antibody, with a pharmaceutically acceptable carrier, or as a mixture with a therapeutic cardiovascular compound to treat hypertrophy, hypertension, congestive heart failure, heart failure subsequent to myocardial infarction, myocardial ischemia, ischemia reperfusion injury, arrhythmia, or myocardial infarction. Preferably the cardiovascular disease treated is congestive heart failure.

Therapeutic cardiovascular compounds that can be concurrently administered with at least one antibody of the invention include an angiotensin converting enzyme inhibitor, an angiotensin II receptor antagonist, a calcium channel blocker, an antithrombolytic agent, a adrenergic receptor antagonist, a vasodilator, a diuretic, an α-adrenergic receptor antagonist, an antioxidant, and a mixture thereof. An antibody of the invention also can be concurrently administered with PPADS (pyridoxal phosphate-6-azophenyl-2',4'-disulphonic acid), also a therapeutic cardiovascular compound, or with PPADS and another known therapeutic cardiovascular compound as already described.

Preferably a therapeutic cardiovascular compound, which is concurrently administered with at least one antibody specific for AC5, a pharmaceutically acceptable carrier thereof, is an angiotensin converting enzyme inhibitor, an angiotensin II receptor antagonist, or a diuretic. Still preferably, the therapeutic cardiovascular compound is an α-adrenergic receptor antagonist. Also preferably, the therapeutic cardiovascular compound is a calcium channel blocker.

These therapeutic cardiovascular compounds are generally used to treat cardiovascular and related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of, for example, angiotensin converting enzyme inhibitor, an angiotensin II receptor antagonist, a calcium channel blocker, an antithrombolytic agent, a β-adrenergic receptor antagonist, a diuretic, an .alpha.-adrenergic receptor antagonist, or a mixture thereof. In some instances, congestive heart failure can be treated by the administration of, for example, angiotensin converting enzyme inhibitor, an angiotensin II receptor antagonist, a calcium channel blocker, a vasodilator, a diuretic, or a mixture thereof.

Myocardial infarction can be treated by the administration of, for example, angiotensin converting enzyme inhibitor, a calcium channel blocker, an antithrombolytic agent, a β-adrenergic receptor antagonist, a diuretic, an α-adrenergic receptor antagonist, or a mixture thereof.

Hypertension can be treated by the administration of, for example, angiotensin converting enzyme inhibitor, a calcium channel blocker, a β-adrenergic receptor antagonist, a vasodilator, a diuretic, an β-adrenergic receptor antagonist, or a mixture thereof.

Moreover, arrhythmia can be treated by the administration of, for example, a calcium channel blocker, a β-adrenergic receptor antagonist, or a mixture thereof.

Antithrombolytic agents are used for reducing or removing blood clots from arteries.

Hypertrophy can be treated by the administration of, for example, an angiotensin converting enzyme inhibitor, an angiotensin II receptor antagonist, a calcium channel blocker, or a mixture thereof.

Ischemia reperfusion injury can be treated by the administration of, for example, an angiotensin converting enzyme inhibitor, an angiotensin II receptor antagonist, a calcium channel blocker, or a mixture thereof.

Known angiotensin converting enzyme inhibitors include, for example, captopril, enalapril, lisinopril, benazapril, fosinopril, quinapril, ramipril, spirapril, imidapril, and moexipril.

Examples of known angiotensin II receptor antagonists include both angiotensin I receptor subtype antagonists and angiotensin II receptor subtype antagonists. Suitable antiotensin II receptor antagonists include losartan and valsartan.

Suitable calcium channel blockers include, for example, verapamil, diltiazem, nicardipine, nifedipine, amlodipine, felodipine, nimodipine, and bepridil.

Antithrombolytic agents known in the art include antiplatelet agents, aspirin, and heparin.

Examples of known α-adrenergic receptor antagonists include atenolol, propranolol, timolol, and metoprolol.

Suitable vasodilators include, for example, hydralazine, nitroglycerin, and isosorbide dinitrate.

Suitable diuretics include, for example, furosemide, diuril, amiloride, and hydrodiuril.

Suitable α-adrenergic receptor antagonists include, for example, prazosin, doxazocin, and labetalol.

Suitable antioxidants include vitamin E, vitamin C, and isoflavones.

At least one AC5 specific antibody, a pharmaceutically acceptable carrier and a therapeutic cardiovascular compound can be administered concurrently. "Concurrent administration" and "concurrently administering" as used herein includes administering a compound of the invention and a therapeutic cardiovascular compound in admixture, such as, for example, in a pharmaceutical composition or in solution, or as separate compounds, such as, for example, separate pharmaceutical compositions or solutions administered consecutively, simultaneously, or at different times but not so distant in time such that the compound of the invention and the therapeutic cardiovascular compound cannot interact and a lower dosage amount of the active ingredient cannot be administered.

Treatment of Neurological Disorders

The striatum is known to coordinate motor function of the body via receiving dopamingeric input that activates the striatal AC. Thus, the regulation of AC5, a major effector enzyme of the dopamine receptor in the striatum, may regulate motor function. Unlike dopamine receptors that are widely expressed, AC5 expression is limited to the striatum within the brain, and not readily detectable in other parts of the brain. The dopamine or beta-adrenergic receptors (β-AR) may undergo desensitization or massive down regulation under pathological conditions, leading to the loss of the receptor on the neuronal cell surface, while changes in AC5 expression is slow and the magnitude of changes is small. Accordingly, AC5 specific regulators, including antibodies to AC5, might replace beta-adrenergic receptor blockers, which are most commonly used to treat hypertension but are contraindicated in asthma patients because tracheal beta-adrenergic receptors are also blocked. In addition, AC5 specific regulators might replace dopamine receptor regulators, which are commonly used to treat Parkinson's disease, the most common motor function disease among the elderly. However, a major problem is the development of tolerance after chronic usage of this medication, which is most likely due to the changes at the level of dopamine receptors. The underlying hypothesis is that the AC5 isoform bears a distinct physiological role in the striatum to regulate motor function, either stimulatory or inhibitory. Disruption of such an AC isoform leads to impaired organ function that is directly or indirectly related to the unique property of this AC isoform. Therefore, establishing a method to regulate this isoform in a specific manner will lead to the regulation of its specific function in the striatum.

Furthermore, the present invention also relates to methods of treating neurodegenerative diseases through enhanced delivery of neuroprotective or neuroenhancing agents that may be efficacious in restoring motor function in subjects suffering from diseases that result in motor dysfunction. Delivery of such agents may be accomplished through coupling of the agent using standard chemical coupling procedures to the AC5 antibodies of the present invention. Such diseases may include Parkinson's disease as well as other conditions that result in loss of motor function and control, such as multiple sclerosis and amyotrophic lateral sclerosis (ALS), as well as viral diseases of the central nervous system of humans and domestic animals, such as post-infectious encephalomyelitis, or prophylactically inhibiting the initiation or progression of demyelination in these disease states, using the strategy of targeting effective drugs with the monoclonal antibody described herein. Drugs that may be delivered by way of the AC5 antibodies may include dopamine agonists and forskolin like agonists.

Diagnostic and Screening Methods

The present invention also relates to methods for screening or diagnosis of a cardiac condition in a subject suspected of having such condition. The subject can be any animal, but preferably the subject is a mammal, and most preferably the subject is a human. In a non-limiting example, the antibodies of the invention can be used as diagnostic probes to determine expression levels of the AC5 gene or gene product and variants thereof. For example, the antibody may be labeled with a radioactive element, an enzyme, a fluorophore or a chromophore. Alternatively, nucleotide probes specific for AC5 may be used to identify tissues and cells expressing the AC5 gene using methods known to one skilled in the art, such as, but not limited to, in situ hybridization.

In addition, the present invention provides for a method for screening, diagnosis or prognosis of a cardiac condition selected from the group consisting of congestive heart failure, cardiac hypertrophy, ischemic heart disease, myocardial infarction, hypertension, arrhythmias, aging cardiomyopathy, idiopathic cardiomyopathy and angina, said method comprising:

(I) measuring an amount of the AC5 gene or gene product in a tissue sample derived from the subject, wherein said AC5 gene or gene product is:
(a) a DNA encoding adenylyl cyclase 5, or a nucleic acid derived therefrom;
(b) a protein comprising adenylyl cyclase 5;
(c) a nucleic acid comprising a sequence hybridizable to adenylyl cyclase 5, or its complement under conditions of high stringency, or a protein comprising a sequence encoded by said hybridizable sequence;
(d) a nucleic acid at least 90% homologous to adenylyl cyclase 5, or its complement as determined using the NBLAST algorithm; or a protein encoded thereby; and (II) comparing the amount of said adenylyl cyclase 5 gene product in the subject with the amount of adenylyl cyclase 5 gene product present in a normal, non-damaged cardiac tissue sample or predetermined standard for normal, non-damaged cardiac tissue sample, wherein an elevated amount of said adenylyl cyclase 5 gene product in the subject compared to the amount in the normal, non-damaged cardiac tissue sample or predetermined standard for a normal, non-damaged cardiac tissue sample indicates a risk of developing a cardiac condition in the subject.

Imaging methods, for imaging the localization and/or amounts of AC5 gene products in a patient, are also provided for diagnostic and prognostic use.

The invention provides methods for identifying agents (e.g., chemical compounds, carbohydrates, proteins, peptides, antibodies or nucleotides) that enhance the expression and/or activity of AC5 gene or gene products. These stimulators or agonists of AC5 may be useful for treating neurodegenerative diseases. The invention also provides methods of identifying agents, candidate compounds or test compounds that specifically bind to AC5 and inhibit its activity. These agents would be beneficial in treating cardiac conditions, such as the antibody 19D5.C1. Examples of agents, candidate compounds or test compounds include, but are not limited to, nucleic acids (e.g., DNA and RNA), carbohydrates, lipids, proteins, peptides, peptidomimetics, small organic chemical molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

Antibodies

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, the term "antibody" is any immunoglobulin, including antibodies and fragments thereof, that binds a specific epitope. The term is intended to encompass polyclonal, monoclonal, and chimeric antibodies, the last mentioned described in further detail in U.S. Pat. Nos. 4,816,397 and 4,816,567. Such antibodies include both polyclonal and monoclonal antibodies prepared by known generic techniques, as well as bi-specific or chimeric antibodies, and antibodies including other functionalities suiting them for additional diagnostic use conjunctive with their capability of modulating activity, e.g. that stimulates cardiac function, or that provides neuroprotection. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions know in the art as Fab, Fab', F(ab')$_2$ and F(v).

Fab and F(ab')$_2$ portions of antibody molecules, or antibody fragments, may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chains portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies useful in the present invention can be screened for various properties; i.e., isotype, epitope, affinity, etc. Of particular interest are monoclonal antibodies that exhibit the same activity as agents that enhance cardiac function. Such monoclonals can be readily identified in activity assays such as the models described herein, such as the AC5 knockout model compared to its wild type normal control used to study pressure overload. High affinity antibodies are also useful when immunoaffinity purification of native or recombinant antibodies is possible. Preferably, the antibody used in the diagnostic methods and therapeutic methods of this invention is an affinity purified polyclonal antibody. More preferably, the antibody is a monoclonal antibody (mAb). In addition, it is contemplated for the antibody molecules used herein be in the form of Fab, Fab', F(ab')$_2$ or F(v) portions of whole antibody molecules, or single chain antibodies.

As suggested earlier, the diagnostic method of the present invention comprises examining a cellular or tissue sample by means of an assay including an effective amount of an antibody peptide/protein, preferably an affinity-purified polyclonal antibody, and more preferably a monoclonal antibody. In addition, it is preferable for the antibody molecules used herein be in the form of Fab, Fab', F(ab')$_2$ or F(v) portions or whole antibody molecules. As previously discussed, patients capable of benefiting from this method include those suffering from a cardiac condition such as congestive heart failure, cardiac hypertrophy, ischemic heart disease, myocardial infarction, angina, hypertension, arrhythmias, aging cardiomyopathy, and idiopathic cardiomyopathy. Methods for isolating the antibodies and for determining and optimizing the ability of antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an antibody peptide-binding portion thereof, or the antibody peptide or fragment, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact in the same fashion as the present autoantibodies and their ability to inhibit or promote specified activity in target cells and tissues.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-peptide antibodies are also well-known in the art. See Niman et al., *Proc. Natl. Acad. Sci. USA,* 80:4949-4953 (1983). Typically, the present antibody peptides, or a peptide analog or fragment, is used either alone or conjugated to an immunogenic carrier, as the immunogen in the before described procedure for producing anti-peptide monoclonal antibodies. The hybridomas are screened for the ability to produce an antibody that immunoreacts with the antibody peptide analog and thereby reacts similarly to the antibodies of the present invention.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The antibody preparation in preferably provided in a pharmaceutically acceptable carrier, vehicle or diluent and is administered intravenously, intramuscularly or orally. The antibody is administered in doses and amounts similar to the administration recognized and utilized by the skilled artisan for the administration of clinically adopted antibodies, including IVIG or IGIM or Pentaglobin, or as instructed or advised clinically or by the manufacturer. IgG preparations for use in the present invention are administered in doses of about 0.5 mg/kg to about 1-2g/kg body weight and can be administered as a single dose or in multiple separated doses daily or over the course of days or months. Suitable dosages include 10 mg/kg body weight, 20 mg/kg body weight, 30 mg/kg body weight, 40 mg/kg body weight, 50 mg/kg body weight, 75 mg/kg body weight, 100 mg/kg body weight, 200 mg/kg body weight, 300 mg/kg body weight, 400 mg/kg body weight, 500 mg/kg body weight, 1 g/kg body weight, and 2g/kg body weight In one particular embodiment, the antibody may be administered in a dosage of 10 mg/kg. The polyclonal IgG or IgM immunoglobulin preparations may be administered alone or in combination with other treatments, including but not limited to other compounds or agents for treatment or alleviation of the condition.

The present invention extends to the use and application of the antibodies of the present invention, particularly monoclonal antibodies, including monomers thereof, or mixtures and/or active fragments thereof, characterized by their ability to bind to structures and cells in the heart and brain, in imaging and in vivo diagnostic applications. Thus, the antibodies, by virtue of their ability to bind to structures and cells in the heart and brain, can be utilized via immunofluorescent, radioactive and other diagnostically suitable tags as imaging agents or imaging molecules for the characterization of the heart or brain tissue and the diagnosis, monitoring and assessment of cardiac conditions and diseases of the nervous system, particularly neurodegenerative diseases such as Parkinson's disease, amyotrophic lateral sclerosis, and multiple sclerosis. The antibodies may further be utilized as imaging agents or imaging molecules in the diagnosis, monitoring and assessment of various dementias including Alzheimer's disease. The appropriate and suitable immunofluorescent, radioactive, or other tagging molecules or agents for coupling or attachment to the antibodies for use in in vivo imaging will be well known to and within the skill of the skilled artisan.

The present invention also relates to methods of treating cardiac diseases and conditions in mammals and viral diseases of the central nervous system of humans and domestic animals, such as post-infectious encephalomyelitis, using the monoclonal antibodies, analogs thereof including haptens, active fragments thereof, or a natural or synthetic antibody having the characteristics thereof. Methods of prophylactic treatment using these mAb, active fragments thereof, or other natural or synthetic antibodies having the same characteristics, to inhibit the initiation or progression of cardiac conditions or diseases or for delivery of suitable neuroprotective drugs are also encompassed by this invention.

Figure 2:
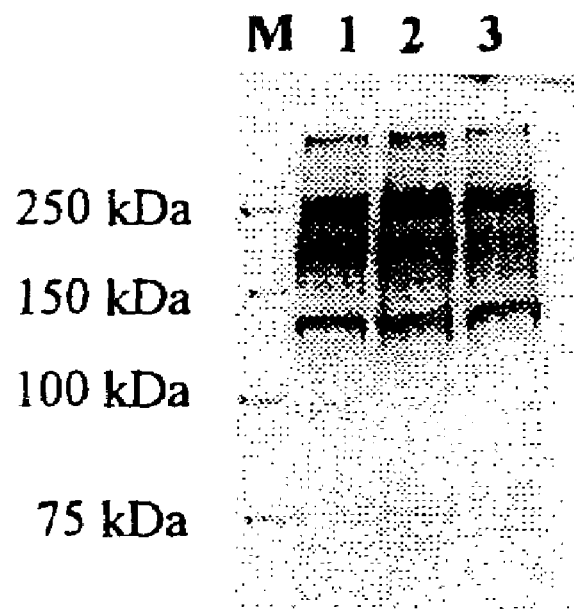
FIG. 2 Western Blot analysis using commercially available ACV/VI antibody with brain tissue derived from 1) AC5 wild type mice; 2) AC5 knock out mice; and 3) AC5 over-expressed mice.

Naturally produced monoclonal antibodies may be generated using classical cloning and cell fusion techniques. In general, the peptide or immunogen is administered (e.g., intraperitoneal injection) to wild-type or inbred mice (e.g., BALB/c) or transgenic mice which produce desired antibodies, or rats, rabbits, chickens, sheep, goats, or other animal species which can produce native or human antibodies. The immunogen may be administered alone, or mixed with adjuvant. After the animal is boosted, for example, two or more times, the spleen or large lymph node, such as the popliteal in rat, is removed and splenocytes or lymphocytes are extracted and fused with myeloma cells using well-known processes, for example Kohler and Milstein [(1975) Nature 256:495-497] and Harlow and Lane [Antibodies: A Laboratory Manual (Cold Spring Harbor Laboratory, New York (1988)]. In the case of the 19D5.C1 monoclonal antibody, a panel of monoclonal antibodies (mAbs) derived from splenocytes of Balb/c mice injected with the peptide of FIG. 3. After the initial fusion and cloning, wells with viable IgG-secreting hybridomas contained mAb with significant binding to AC5 as demonstrated by ELISA. Hybridoma cells from these wells were subcloned by limiting dilution and screened again for binding to AC5 by ELISA. Based upon the ELISA data, the wells showing positive antibody reactivity were chosen for ascites production and in vitro testing. The monoclonal antibodies were then isolated and purified from ascites fluid and tested for binding to AC5 using brain tissue from wild type mice, or from AC5 knockout mice or from mice in which AC5 is overexpressed in the brain, using standard Western blotting techniques. As shown in FIG. 1, the 19D5.C1 monoclonal antibody showed high specificity for the AC5 isoform since no binding was observed in the brain tissue from AC5 knockout mice. A comparative study was conducted using a commercially available polyclonal antibody to AC5/AC6. As shown in FIG. 2, this polyclonal antibody does not exhibit the specificity shown by 19D5.C1, since there are no differences in the binding characteristics to brain tissue from wild type mice, AC5−/− mice, or mice displaying an overexpression of AC5.

Therapeutic and Prophylactic Compositions and Their Use

While it is possible for an antibody or fragment thereof to be administered alone, it is preferable to present it as a pharmaceutical composition. A generally recognized compendium of methods and ingredients of pharmaceutical compositions is Remington's Pharmaceutical Science, 15th ed., Mack Publishing Company, Easton, Pa. The active ingredient may comprise, for topical administration, from 0.001% to 10% w/w, e.g., from 1% to 2% by weight of the composition, although it may comprise as much as 10% w/w but preferably not in excess of 5% w/w and more preferably from 0.1% to 1% w/w of the composition.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical compositions may vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 ml sterile buffered water, and 50 mg of an antibody or fragment thereof of the invention. Similarly, a pharmaceutical composition of the invention for intravenous infusion could be made up to contain 250 ml of sterile Ringer's solution, and 150 mg of an antibody or fragment thereof of the invention. Actual methods for preparing parenterally administrable compositions are well-known or will be apparent to those skilled in the art, and are described in more detail in, e.g., Remington's Pharmaceutical Science, 15th ed., Mack Publishing Company, Easton, Pa.

The antibodies, or fragments thereof, of the invention may be lyophilized for storage and reconstituted in a suitable carrier prior to use. This technique is effective with conventional immunoglobulins and art-known lyophilization and reconstitution techniques may be employed.

The pharmaceutical composition of the invention may be administered for prophylactic and/or therapeutic treatments. In therapeutic application, compositions are administered to a subject already suffering from a cardiac condition or a neurodegenerative disease, in an amount sufficient to cure or at least partially arrest the disorder and its complications. In prophylactic applications, compositions containing the present antibodies or fragments thereof are administered to a subject not already in a disease state but one that may be predisposed to a cardiac condition or neurodegenerative disease to enhance the subject's resistance.

It will be recognized by one of skill in the art that the optimal quantity and spacing of individual dosages of an antibody or fragment thereof of the invention will be determined by the nature and extent of the disorder being treated, the form, route and site of administration, and the particular animal being treated, and that such optimums may be determined by conventional techniques. It will also be appreciated by one of skill in the art that the optimal course of treatment, i.e., the number of doses of an antibody or fragment thereof of the invention given per day for a defined number of days, may be ascertained by those skilled in the art using conventional course of treatment determination tests.

EXAMPLES

Example 1

Generation of antibodies specific for adenylyl cyclase 5 (AC5)

The peptide shown in FIG. 3 was administered by intraperitoneal injection alternating with subcutaneous injection to BALB/c mice. The amount of the peptide delivered was 25 µg per injection. The peptide was initially administered with Titermax, then subsequent injections were made with Freund's incomplete adjuvant. After the mice received 3 to 5 injections of 25 µg each at 2 week intervals, the spleens were removed and splenocytes were extracted and fused with myeloma cells using the procedure described by Kohler and Milstein [(1975) Nature 256:495-497] and Harlow and Lane (Antibodies: A Laboratory Manual Cold Spring Harbor Laboratory, New York (1988)). In the case of the 19D5.C1 monoclonal antibody, a panel of monoclonal antibodies (mAbs) derived from splenocytes of Balb/c mice injected with the peptide of FIG. 3 was constructed as described. After the initial fusion and cloning, wells with viable IgG-secreting hybridomas contained mAb with significant binding to AC5 as demonstrated by ELISA. Hybridoma cells from these wells were subcloned by limiting dilution and screened again for binding to AC5 by ELISA. Based upon the ELISA data, the wells showing positive antibody reactivity were chosen for ascites production and in vitro testing. The monoclonal antibodies were then isolated and purified from ascites fluid and tested for binding to AC5 using brain tissue from wild type mice, or from AC5 knockout mice or from mice in which AC5 is overexpressed in the brain using standard Western blotting techniques.

Western Blots

Western blotting was performed on 8% SDS-PAGE gels at 90 v for 3 hrs. The separated proteins were transferred to PVDF membranes using a semidry transfer apparatus for 90 min. at 100 v. The blots were probed with the 19D5.C1 antibody at 1:1000 dilution at room temperature overnight. Incubation was with an anti-mouse secondary antibody coupled to horseradish peroxidase at 1:2000 dilution for 30 minutes at room temperature. Unbound antibodies were washed and horseradish peroxidase was visualized on x-ray film with an enhanced chemiluminescence detection kit.

Results

As shown in FIG. 1, the 19D5.C1 monoclonal antibody showed high specificity for the AC5 isoform as shown by binding to a protein band having an apparent molecular weight of 250 kDa and since no binding was observed in the brain tissue from AC5 knockout mice. A comparative study was conducted using a commercially available polyclonal antibody to AC5/AC6. As shown in FIG. 2, this antibody does not exhibit the specificity shown by 19D5.C1, since there are no differences in the binding characteristics to brain tissue from wild type mice, AC5−/− mice, or mice displaying an overexpression of AC5.

Example 2

Generation of Knockout Mice

The targeting construct was prepared by ligating a 2.2-kb XhoI-PstI fragment from the 5' end of the type 5 AC gene, containing the exon with the first translation initiation site (5'-arm), a 1.7-kb fragment containing a neomycin resistance gene fragment (neo) driven by a phosphoglycerate kinase (PGK) promoter, and a BssHII-NcoI 7.0-kb fragment of the type 5 AC gene (3'-arm), into pBluscript II KS (Stratagene, La Jolla, Calif., USA) (FIG. 4A). The type 5 AC gene has another translational start site accompanied by a reasonable Kozak consensus sequence located 738-bp downstream of the first translational start site within the same exon. To impair the second site, inventors excised a 0.15 kb PstI-BssHII fragment containing the second ATG and replaced it with a PGK-neo cassette in the final targeting vector (FIG. 4A).

Embryonic stem cells were transfected with 50 µg linearized targeting vector by electroporation (Bio-Rad Gene pulsar set at 250 V and 960° F.). G418 (200 µg/ml) selection was applied 48 hours after transfection and resistant clones were isolated after 7-10 days of transfection. Subsequently, inventors obtained 576 clones. Genomic DNA from these resistant clones was digested with KpnI and probed with a 5' probe. Digesting genomic DNA with BamHI and probing with a 3' probe reconfirmed 8 positive clones. A single integration of the targeting vector was confirmed by a neo-probe. Two clones (clones #314 and #378) were injected into C57BL/6 blastocysts and chimeras were obtained. These chimeras successfully allowed germ-line transmission and were crossed with C57BL/6 females. F1-heterozygous offspring were then interbred to produce homozygous mutations. All mice were 129/SvJ-C57BL/6 mixed background litter mates from F1 heterozygote crosses. All experiments were performed in 4-6 month old homozygous AC5KO and wild-type (WT) littermates. This study was approved by the Animal Care and Use Committee at New Jersey Medical School.

RNase Protection Assay

Partial fragments of mouse AC cDNA clones for each isoform (types 1-9) were obtained by PCR. Sequencing and restriction mapping verified these cDNA fragments. Total RNA was isolated using RNeasy Midi kit (QIAGEN, Valencia, Calif., USA). Single strand cDNA was synthesized from total RNA using reverse transcriptase. The plasmid constructs were linearized by appropriate restriction enzyme. $^{32}$P-labeled cRNA probes were then generated using the Riboprobe Systems (Promega, Madison, Wis., USA). A human 28S ribosomal RNA probe was used as an internal control. RNase protection assay was performed using the RPA III kit (Ambion, Austin, Tex., USA) as suggested by the manufacture, followed by analysis on a 5% polyacrylamide-urea gel. Gels were exposed to X-OMAT film (Kodak, Rochester, N.Y., USA) for quantitation.

AC Assay and Tissue Camp Measurement

Hearts were dissected from the mice and membrane preparations were prepared as described previously (Ishikawa, Y., Sorota, S., Kiuchi, K., Shannon, R. P., Komamura, K., Katsushika, S., Vatner, D. E., Vatner, S. F., and Homcy, C. J. (1994), J. Clin. Invest. 93:2224-2229.). Protein concentration was measured by the method of Bradford using bovine serum albumin as a standard (Bradford, M. M. (1976). Anal. Biochem. 72:248-254.). AC activity was measured as described previously (Kawabe, J., Iwami, G., Ebina, T., Ohno, S., Katada, T., Ueda, Y., Homcy, C. J., and Ishikawa, Y. (1994), J. Biol. Chem. 269:16554-16558). AC activity was linear within the incubation time up to 30 min. In order to harvest hearts for tissue cAMP content measurements, mice were allowed to acclimate to the surroundings in the laboratory for an hour before sacrifice. Freshly isolated hearts were briefly immersed in liquid nitrogen. The tissue was homogenized in ice-cold 6% percholic acid, and cAMP was extracted as described before (Kawabe, J., Aizawa, Y., Takehara, N., Hasebe, N., and Kikuch, K. (2000), J. Hypertens. 18:1457-1464). The concentration of cAMP was determined with an RIA kit (PerkinElmer Life Sciences, Boston, Mass., USA).

Physiological Studies

Adenylyl cyclase 5 knockout (AC5KO) mice (6.4±0.2 month old, n=6) and wild type (WT) mice (6.7±0.1 month old, n=6) of either sex from the same genetic background as the transgenic mice were used for the physiological studies. Measurements of LV ejection fraction (LVEF) were performed as described previously (Iwase, M., Uechi, M., Vatner, D. E., Asai, K., Shannon, R. P., Kudej, R. K., Wagner, T. E., Wight, D.C., Patrick, T. A., Ishikawa, Y., et al. (1997), Am. J. Physiol. 272:H585-589.). Briefly, after determination of body weight, mice were anesthetized with ketamine (0.065 mg/g), acepromazine (0.002 mg/g), and xylazine (0.013 mg/g) injected intraperitoneally and were allowed to breathe spontaneously. Echocardiography was performed using ultrasonography (Sequoia C256; Acuson Corporation, Mountain View, Calif., USA). A dynamically focused 15-MHz annular array transducer was applied from below, using a warmed saline bag as a standoff. M-mode echocardiographic measurements of the LV were performed at baseline and during intravenous infusion of ISO (0.005, 0.01, 0.02, and 0.04 µg/kg/min i.v. for 5 minutes each)(Abbott Laboratories Inc, North Chicago, Ill., USA) using an infusion pump (PHD 2000; Harvard Apparatus, Inc., Holliston, Mass., USA). The total amount of the infusion volume was <100 µL in each mouse. On a separate occasion, each mouse received an infusion of saline as a control to ensure that the volume of infusion alone did not contribute to enhance ventricular performance. To examine the responses to a muscarinic agonist, acetylcholine (Ach) was co-administered intraperitoneally (i.p. 25 mg/kg) during i.v. infusion of ISO (0.04 µg/kg/min).

In AC5KO and WT mice, four ECG wires (New England Electric Wire Corporation, Lisbon, N.H., USA) were placed subcutaneously, a silicone elastomer tubing (Cardiovascular Instrument Corp., Wakefield, Mass., USA) was inserted into the right external jugular vein and a 1.4 F micromanometer catheter (Millar Instruments, Inc., Houston, Tex., USA) was inserted into the lower abdominal aorta via the femoral artery as described previously with some modifications (Uechi, M., Asai, K., Osaka, M., Smith, A., Sato, N., Wagner, T. E., Ishikawa, Y., Hayakawa, H., Vatner, D. E., Shannon, R. P., et al. (1998), Circ. Res. 82:416-423). The ECG wires, the silicone elastomer tubing and the micromanometer catheter were tunneled subcutaneously to the back, externalized, and secured in a plastic cap. On the day of the study, each mouse was placed in the mouse holder, the jugular venous catheter was accessed and connected to a microliter syringe (Hamilton Co., Reno, Nev., USA), the 1.4 F micromanometer catheter was connected to a recorder (Dash 4u; Astro-Med, Inc., West Warwick, R.I., USA) and the ECG wires were connected to an ECG amplifier (Gould Inc., Cleveland, Ohio, USA). All experiments were recorded with animals in the conscious state. After at least 6 hours recovery from the implantation of the catheter, when a stable HR was achieved, the baseline ECG and arterial pressure (AP) were recorded for 5 min. Ach(0.05 µg/g) was then administered intravenously (i.v.), and the ECG and AP recording were repeated. A recovery period of 15 min was allowed for the HR and AP to return to baseline before administering the next drug. Baseline HR slowing was examined in response to phenylephrine (0.2 µg/g i.v.).

Statistics

All data are reported as mean ±SEM. Comparisons between AC5KO and WT values were made using a students t-test. P<0.05 was taken as a minimal level of significance.

Results:

Targeted Disruption of the Type 5 AC Gene.

The type 5 AC gene was disrupted in mice using homologous recombination (FIG. 4a). Mice were genotyped by Southern blotting using genomic DNA from tail biopsies (FIG. 4b). mRNA expression of the type 5 AC in heterozygous mice was approximately half of that in WT and it was undetectable in AC5KO (FIG. 4c). The growth, general appearance and behavior were similar to those of WT.

No Compensatory Increase in the Other Isoforms of AC

Inventors then examined whether there were compensatory increases in the expression of the other isoforms of AC in AC5KO. Since AC isoform antibodies that can convincingly determine the level of protein expression of all the isoforms are not available, inventors quantitated the mRNA expression of the AC isoforms by an RNase protection assay. cRNA of the 28S ribosomal RNA was used as an internal control. Types 3, 4, 6, 7 and 9 AC were readily detected, but not increased (FIG. 4d), while types 1, 2, and 8 were hardly detectable (data not shown), indicating that type 6 AC, a homologue of type 5 AC in the heart, could not compensate for the type 5 AC deficiency.

AC Activity was Decreased in the Hearts of AC5KO In Vitro

Figure 5:
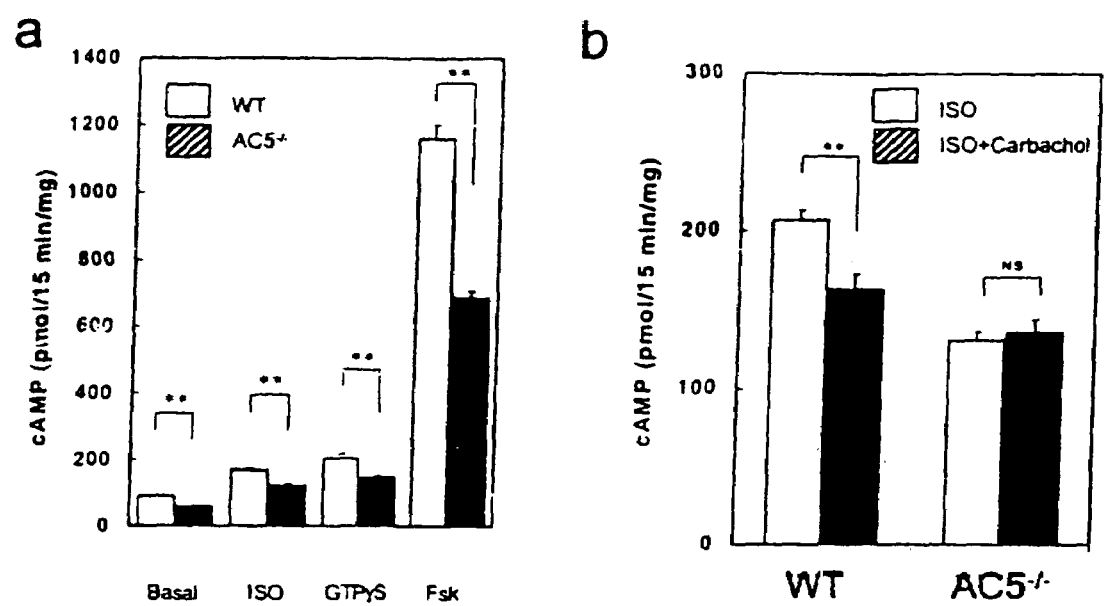
FIG. 5b): Comparison of inhibition of ISO-stimulated AC activity in WT and AC5KO in the presence of carbachol (10 μM) (a muscrarinic agonist).

Inventors then examined cAMP production in membranes from the hearts of AC5KO and WT at 6 months of age (FIG. 5A). The steady state AC activity was determined as the maximal capacity of cAMP production in the presence of ISO (100 µM ISO+100 µM GTP), GTPγS (100 µM) or forskolin (100 µM). AC activity was decreased in AC5KO relative to that in WT by 35±4.3% (basal), 27±4.6% (ISO), 27±2.4% (GTPµS), and 40±4.7% (forskolin). These data indicate that type 5 AC, as the major isoform in the heart, is responsible for approximately 30-40% of total AC activity in the mouse heart. However, cardiac tissue cAMP content was not significantly decreased in AC5KO compared to WT (55±7.5 vs 62±3.4 pmol/mg protein, respectively, n=4, p=NS). Carbachol (10 µM), a muscarinic agonist, decreased ISO-stimulated AC activity by 21±3.4% in WT, but did not inhibit ISO-stimulated AC activity in AC5KO (FIG. 5B).

Figure 6:
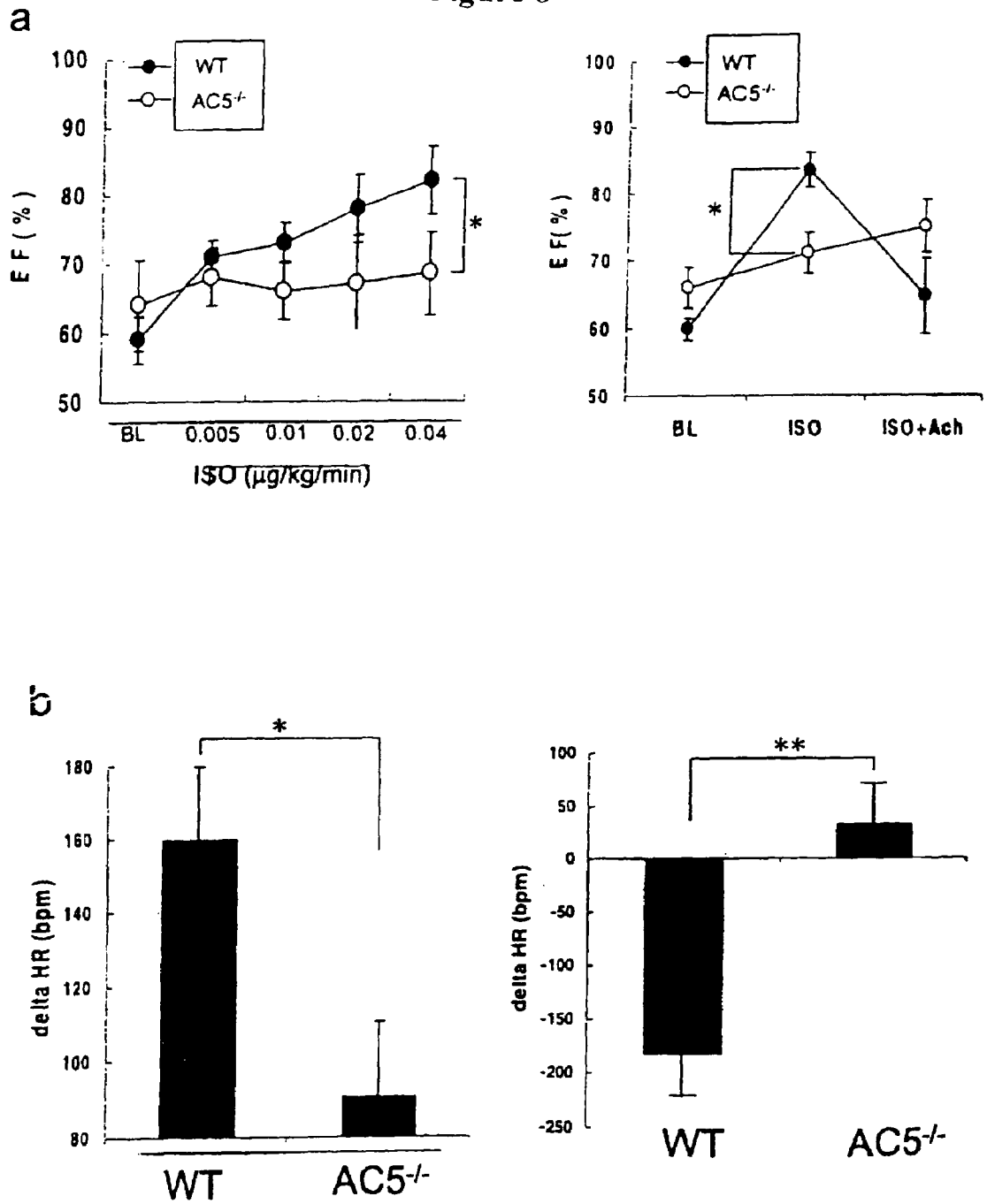
FIG. 6A: Comparison of basal and ISO stimualted cardiac function in WT and AC5KO.
FIG. 6B: Parasympathetic control of Heart Rate in WT and AC5 KO.

Basal Cardiac Function was not Decreased, But the Response to ISO and Muscarinic Inhibition of ISO were Attenuated Inventors originally hypothesized that cardiac function, both basal and ISO-stimulated, would be depressed. The cardiac responses to i.v. ISO on LVEF and fractional shortening (FS) in AC5KO were attenuated as expected (FIGS. 6a and b). However, baseline cardiac function tended to be increased; LVEF (WT vs. AC5KO; 59±2.4% vs. 64±4.3%) and FS (26±1.4% vs. 29±2.7%). Muscarinic inhibition of ISO stimulated cardiac function, as measured by LVEF, was prominent in WT, as expected, but was abolished in AC5KO (FIG. 6a).

Parasympathetic (Muscarinic) Control of HR.

Figure 7:
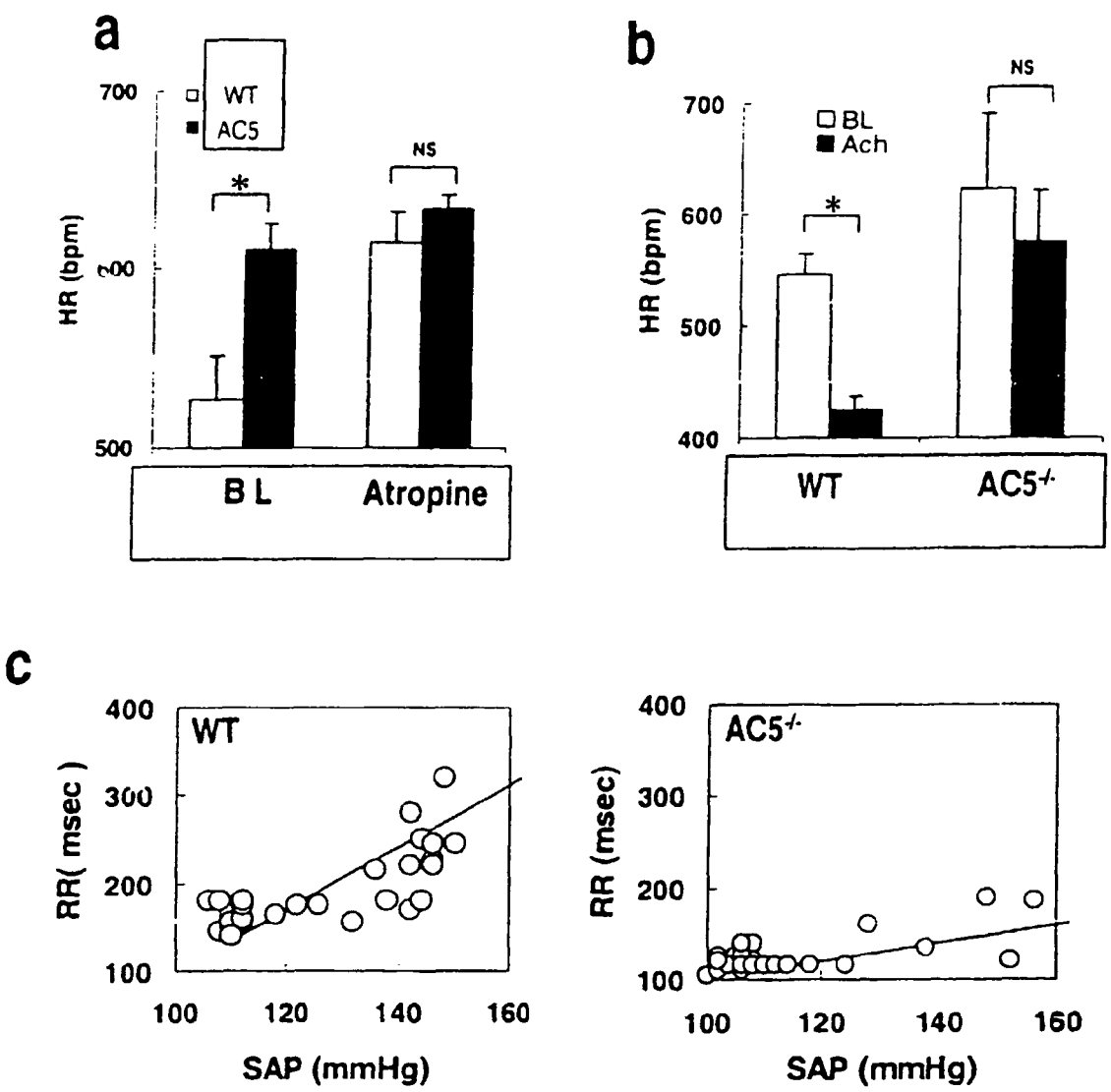
FIGS. 7A, 7B, and 7C: Comparison of Heart Rate in WT and AC5KO under muscarinic stimulation with atropine.

In the presence of ISO, Ach reduced HR in WT, but not in AC5KO (FIG. 6b). Baseline HR was significantly elevated in conscious AC5KO (FIG. 7a). Muscarinic stimulation in conscious WT with Ach (0.01 µg/g i.v.) decreased HR by 22% but significantly less (7.5%) in AC5KO (FIG. 7b). Phenylephrine (0.2 µg/g i.v.) increased systolic arterial pressure significantly in both WT and AC5KO, but induced less baroreflex mediated slowing of HR in AC5KO than in WT (FIG. 7c). The increase in HR following atropine (1 µg/g i.v.), in WT (102±22.2 beats/min) was not observed in AC5KO (19±7.5 beats/min) (FIG. 7a).

AC is critical to regulating cardiac contractility and rate, particularly in response to sympathetic activation (Homcy, C. J., Vatner, S. F., and Vatner, D. E. (1991), Annu. Rev. Physiol. 53:137-159). The rate of cardiac contraction is also under sympathetic control, but parasympathetic mechanisms may be even more important in its regulation, particularly with regard to reflex cardiac slowing (Higgins, C. B., Vatner, S. F., and Braunwald, E. (1973), Pharmacol. Rev. 25:119-155). Importantly, AC is involved in parasympathetic modulation of cardiac function and HR, particularly in the presence of sympathetic stimulation.

A key mechanistic approach to understanding the role of AC in vivo is to alter AC genetically in the heart. Previous studies have overexpressed types 5, 6 and 8 AC in the heart (Tepe, N. M., Lorenz, J. N., Yatani, A., Dash, R., Kranias, E. G., Dorn, G. W., 2nd, and Liggett, S. B. (1999), Biochemistry 38:16706-16713; Gao, M. H., Lai, N. C., Roth, D. M., Zhou, J., Zhu, J., Anzai, T., Dalton, N., and Hammond, H. K. (1999) Circulation 99:1618-1622; Lipskaia, L., Defer, N., Esposito, G., Hajar, I., Garel, M. C., Rockman, H. A., and Hanoune, J. (2000), Circ. Res. 86:795-801). These studies found the expected increases in response to β-AR stimulation, but failed to observe any changes in parasympathetic control. Although targeted disruption of cardiac AC would be the preferred experimental approach to understand the mechanistic role of AC in the heart, this has not been accomplished previously. Some of the reasons are simply technical difficulties in producing the knockout. More importantly, there is not one AC, but rather 9 mammalian membrane-bound AC isoforms (Hanoune, J., and Defer, N. (2001), Annu. Rev. Pharmacol. Toxicol. 41:145-174) and significant heterogeneity exists in their distribution and biochemical properties, such that function of the isoforms may differ even within the same tissue (Hanoune, J., and Defer, N. (2001), Annu. Rev. Pharmacol. Toxicol. 41:145-174; Ishikawa, Y., and Homcy, C. J. (1997), Circ. Res. 80:297-304). Storm's laboratory deleted types 1, 3 and 8 AC, but the effects on cardiac function were not delineated (Wu, Z. L., Thomas, S. A., Villacres, E. C., Xia, Z., Simmons, M. L., Chavkin, C., Palmiter, R. D., and Storm, D. R. (1995), Proc. Natl. Acad. Sci. USA 92:220-224; Wong, S. T., Trinh, K., Hacker, B., Chan, G. C., Lowe, G., Gaggar, A., Xia, Z., Gold, G. H., and Storm, D. R. (2000), Neuron 27:487-497; Watson, E. L., Jacobson, K. L., Singh, J. C., Idzerda, R., Ott, S. M., DiJulio, D. H., Wong, S. T., and Storm, D. R. (2000), J. Biol. Chem. 275:14691-14699). Inventors selected type 5 AC for deletion in this investigation, since this is the major AC isoform in the adult heart (Tobise, K., Ishikawa, Y., Holmer, S. R., Im, M. J., Newell, J. B., Yoshie, H., Fujita, M., Susannie, E. E., and Homcy, C. J. (1994), Circ. Res. 74:596-603; Espinasse, I., Iourgenko, V., Defer, N., Samson, F., Hanoune, J., and Mercadier, J. J. (1995), J. Mol. Cell. Cardiol. 27:1789-1795.), which was confirmed in cardiac membrane preparations from AC5KO, where 30-40% of AC activity was lost. In addition, its biochemical properties reflect the overall signature of cardiac AC, in that types 5 and 6 are sensitive to direct inhibition by Gi (Hanoune, J., and Defer, N. (2001), Annu. Rev. Pharmacol. Toxicol. 41:145-174; Taussig, R., Iniguez-Lluhi, J. A., and Gilman, A. G. (1993), Science 261:218-221; Dessauer, C. W., Tesmer, J. J., Sprang, S. R., and Gilman, A. G. (1998), J. Biol. Chem. 273:25831-25839).

It was predictable that increases in cardiac function and rate in response to ISO would be diminished in AC5KO, as was demonstrated in this study. Similarly, inventors had expected that baseline cardiac function and HR would be reduced in AC5KO. This was not observed. In fact, baseline LVEF tended to be increased, and HR was significantly elevated in conscious AC5KO. Autonomically-mediated increases in HR can be attributed to increased sympathetic tone or reduced parasympathetic tone. Since the elevated HR was not likely due to enhanced sympathetic tone, i.e., inventors had already demonstrated that sympathetic responses were attenuated in AC5KO, inventors hypothesized that it was due to loss of parasympathetic inhibition. Inventors addressed this hypothesis with several experiments. First, inventors demonstrated that muscarinic inhibition was reduced in AC5KO in the presence of enhanced β-AR stimulation with ISO. Inventors observed neither the reduction in EF nor the decrease in HR induced by Ach in the presence of ISO in AC5KO, whereas both effects were pronounced in the WT. Inventors next determined the effects of muscarinic stimulation in the absence of enhanced sympathetic stimulation. Inventors reasoned that these experiments would be best conducted in the conscious state. As already noted, in conscious AC5KO mice, HR is significantly elevated at baseline, which should facilitate an experiment with the object of demonstrating a decrease in HR. Muscarinic stimulation with Ach elicited the expected prominent decline in HR in WT, but a significantly blunted bradycardia in AC5KO. Conversely, atropine increased HR in WT, but not in AC5KO.

The above experiments indicate that muscarinic inhibition of HR in AC5KO is impaired, but do not demonstrate that this mechanism plays a role, in vivo, under conditions of enhanced parasympathetic tone. Perhaps the most intense parasympathetic tone can be elicited by activating reflex mechanisms. The best characterized reflex is the arterial baroreflex, which responds to an elevation in arterial pressure with bradycardia, mediated predominantly by parasympathetic mechanisms in the conscious animal (Vatner, S. F., and Braunwald, E. (1972). Prog. Cardiovasc. Dis. 14:431-445; Higgins, C. B., Vatner, S. F., and Braunwald, E. (1973), Pharmacol. Rev. 25:119-155). In WT, arterial pressure elevation with phenylephrine elicited intense bradycardia, which was blunted significantly in the AC5KO, indicating that parasympathetic mediation of reflex HR is impaired in AC5KO. These data taken together, provide convincing evidence in vivo that type 5 AC exerts a major role in parasympathetic regulation of cardiac function, in addition to its key role in sympathetic regulation, which has been recognized for some time. Thus, cAMP-mediated parasympathetic modulation of ventricular function and atrial function, i.e., HR, must be considered along with the more widely recognized mechanisms involving muscarinic modulation of potassium channel activity (Yatani, A., Codina, J., Brown, A. M., and Birnbaumer, L. (1987), Science 235:207-211).

In summary, the AC5KO mouse provides an excellent model to study AC isoform specific regulation of the heart. The in vitro experiments confirmed that type 5 AC is the major isoform in the heart, and that in vivo, ISO stimulation of cardiac function and rate were blunted. Since type 5 AC is the major AC isoform expressed in the adult mouse heart, it was surprising to find no effect on baseline cardiac function, but rather an increase in HR, despite reduced baseline AC activity. Paradoxically, the increased basal HR, is more likely related to a loss of parasympathetic restraint, since loss of sympathetic stimulation would act in the opposite direction. The blunted parasympathetic restraint was also observed in response to baroreflex mediated bradycardia, and conversely, atropine induced less tachycardia in the AC5KO than in the WT. Thus, type 5 AC regulates cardiac inotropy and chronotropy through both the sympathetic and parasympathetic arms of the autonomic nervous system.

Example 3

Motor Dysfunction in AC5KO Mice

The striatum receives neuronal input from the cortex, feed backing its signal to the thalamus and cortex via the substantia nigra to coordinate extra-pyramidal signal and regulate motor function. Neuronal activity of the striatum is modulated by dopaminergic neurons that are derived from the substantia nigra. Dopamine receptors in the striatum, both D1 and D2 subtypes, are coupled to AC via G protein to modulate cAMP signal within the striatum. Degeneration of these nigro-striatal neurons, ie, the loss of dopaminergic input to the striatum, is a hallmark of pathological changes seen in Parkinson's disease, which is represented by bradykinesia, tremor and the loss of coordinated movements. Parkinson's disease is a common disease among the elderly, only next to Alzheimer's disease. The nature of this neuronal dysfunction, however, is poorly understood. Previous studies demonstrated that alteration of dopaminergic signal, such as the depletion of dopamine, produce a motor dysfunction that mimics Parkinson's disease, which can be restored by administration of dopamine.

The neurotransmitter dopamine acts through various dopaminergic receptor subtypes that are associated with either stimulation or inhibition of adenylyl cyclases (AC), leading to the regulation of physiological functions such as the control of various motor functions or psychomotor activity. This dopamine-sensitive AC activity is highest in the striatum as well as in associated limbic structures of the brain, where their levels of activity by orders of magnitude exceed those in other areas of the brain. Such differences in striatal enzymatic activity may be attributed to the amount and/or combination of the enzyme isoforms that are expressed differentially in each brain region. The brain expresses all nine AC isoforms (AC1-AC9) that have distinct biochemical properties, i.e., regulation by Gi, Gβγ, calcium, or various kinases. Most, if not all, isoforms are enriched in specific brain regions, rather than diffusely distributed throughout the brain. AC5, for example, is the dominant isoform in the striatum as well as in the heart. However, the coupling of each enzyme isoform to a specific neuronal function or functions, and a receptor signal remains unknown, as does whether the function of an AC isoform, unlike that of the receptors, can be substituted by another isoform.

The striatum is considered to be the center of sensorimotor integration within the basal ganglia and receives widespread excitatory input from all regions of the cortex that converge with extensive dopaminergic, both D1 and D2, afferent from the midbrain. Concerted and balanced activity of these two dopaminergic signals is believed to play a key role in regulating striatal motor functions. In this study, the inventors examined the role of their potential target enzyme isoform, AC5, by the use of knockout mice in which the AC5 gene was disrupted.

Experimental Procedures

Generation of AC5 Knockout (AC5KO) Mice

The AC5 gene was disrupted in mice using the homologous recombination technique (AC5KO) as described above. Mice were genotyped by Southern blotting using genomic DNA from tail biopsies. There was no gross tissue abnormality (data not shown). All the comparisons were made between littermates of AC5KO and wild type (WT).

RNase Protection Assay

Partial fragments of mouse AC cDNA clones for each isoform (types 1-9) and neutopeptides, i.e., enkephalin, substance P, dynorphin, were obtained by PCR. A human 28S ribosomal RNA probe was used as an internal control. RNase protection assay was performed using the RPA III kit (Ambion, Austin, Tex., USA).

AC Assay

Striatal tissues were dissected from mice and membrane preparations were prepared for AC assays as previously described (Hess, E. J. et al. (1987), Mol. Pharmacol. 31, 50-57; Ishikawa, Y. et al. (1994); J. Clin. Invest. 93:2224-2229).

Cyclic AMP Accumulation Assays

Reaction with various agonists in the presence of a phosphodiesterase inhibitor proceed for 10 minutes and are stopped by the addition of ice-cold 2.5% perchloric acid, followed by sonication and centrifugation. Pellets are dissolved in 0.1 N NaOH for protein measurements and the supernatants are subject to cAMP assay by radioimmunoassay after neutralization.

Restoration of Motor Function with cAMP or db-cAMP

If the striatal depletion of cAMP causes motor dysfunction, the inventors postulated that administration of cAMP may restore motor function. Alternatively, if the attenuation of either D1 or D2 dopaminergic signal is responsible for motor dysfunction, selective stimulation of dopaminergic receptor subtypes may restore motor functions. A membrane-permeable analog of cAMP, db-cAMP was injected into mice intra peritoneally and intracranially. Intraperitoneal injection may be preferred to intravenous injection because of the slow absorption and potentially longer lasting effect, allowing enough time to carry out motor function test. Intracranial injection has an advantage that the elevation of cAMP concentration occurs only in the striatum. Also under consideration was the injection of dopamine receptor subtype agonists, which are clinically used in the treatment of Parkinson's disease, and forskolin analogs that have an increased selectivity to a specific AC isoform.

The animals were tested for motor function 30 minutes after i. p. administration of 10 mg/kg of db-cAMP. The test was repeated after 48 hours of drug administration when the drug effect was completely eliminated. Similarly, intracranial injection of db-cAMP was conducted. Before drug injection, the mice were anesthetized with ketamine. Injections of db-cAMP into the mouse brain were performed at the following coordinates: for injection into the striatum: 1.70 mm anterior to the bregma, 1.1 mm to the right of the midline, and 4.1 mm deep. Three micro-liters of drug solution was loaded into an internal cannula needle (C315×33) with cannula tubing connected to a Hamilton syringe mounted onto a microinjection pump (Harvard Apparatus, Dover, Mass.). The drug solutions were delivered at a rate of 0.5 μl/min. Normal saline was injected in a sham control.

Receptor Stimulated cAMP Production

To examine whether AC5 plays a major role in regulating cAMP production, receptor-stimulated cAMP production and its effect in the striatum was measured. The rationale for this study is as follows. Changes in cAMP signal upon receptor stimulation can be easily determined by measuring AC activity in intact neuronal cells because the striatal membrane preparations present a few problems. Determination of basal, GTPγS— and forskolin-stimulated AC activity may be readily done while receptor-regulated AC activity, both stimulatory and inhibitory, is not easy in the striatum. This is, at least partially, due to less abundant receptor expression and the disruption of the receptor/G protein/AC coupling during the process of membrane homogenization of the striatum. Therefore, the effect of receptor stimulation and its sequential changes in AC activity and further downstream events including the process of phosphorylation/dephosphorylation may be best examined using cultured cells or even the whole body. Preliminary studies were done in WT mice using D1 dopaminergic agonists (dopamine and forskolin) to evaluate whether AC5 activity could be stimulated to increase production of cAMP, thus enhancing neuronal function.

Primary Striatal Culture

Striatal neurons are cultured as described herein. Striatum is dissected from embryonic pus on embryonic day 18 and will be placed in D1 saline (100 U/ml papain, 100 mM $CaCl_2$, 50 mM EDTA, and 1.5 mM NaOH) for 15 min at 37° C., washed for 5 min with 10 FC (10% fetal calf serum, 50U/ml penicillin/streptomycin, 4 mM glutamine) in minimum essential media containing trypsin inhibitor and bovine serum albumin. Cells are dissociated in 10FC and plated in six-well plates in neurobasal media (B27 supplement, Life Technologies, Gaithersburg, Md.; 0.5 mM L-glutamine; and 25 µM glutamate) on astrocytes prepared identically but plated in 10FC and treated with 5'fluoro-2'deoxyuridine (mitotic inhibitor). Neurons are fed with neurobasal media without glutamate on days 3 and 7, and cAMP assays are performed between days 4 and 8.

Radioligand Binding Assay

D1 and D2 dopaminergic receptor binding assays were performed using $^3$H-SCH23390 and $^3$H-spiperone, respectively, as previously described (Hess, E. J. et al. (1986), Eur. J. Pharmacol. 121: 31-38; Baik, J. H., (1995), Nature 377: 424-428). Preliminary experiments demonstrated the Kd and Bmax values for D1 and D2 dopaminergic receptors were similar to those previously reported (Hess, E. J. et al. (1986), Eur. J. Pharmacol. 121: 31-38; Baik, J. H., (1995), Nature 377: 424-428).

Behavioral Tests

Motor functions of mice were assessed by rotor rod test (Brandon, E. P., (1998), J. Neuroscience 18: 3639-3649), locomotor activity tests (Brandon, E. P., (1998), J. Neuroscience 18: 3639-3649; Krezel, W. et al. (1998), Science 279:863-867), pole test (Matsuura, K. et al., (1997), J. Neurosci Methods 73:45-48), and tail suspension test (Yamamoto, A. et al. (2000), Cell 101: 57-66).

Rotor Rod Test

The rotor rod test is the most commonly used method to evaluate the motor function in rodents[106] but other methods are also available[107] to reinforce the findings of the rotor rod test. Such tests include rearing test, spontaneous movement study and pole test. The first test examines the frequency of vertical movements of mice and the second examines that of horizontal movements. Thus, spontaneous activity was determined both horizontally (locomotion) and vertically (rearings). The last test, the pole test, examines the degree of bradykinesia. In this test, mice were placed head upward on the top of a rough-surfaced pole. The time until they turned downward (Tturn) and the time until they climbed down to the floor were measured (TLA). Mice were placed in a cage and their movements were videotaped for analysis. Thus, spontaneous movements as an index of motor function were evaluated. Most important, these tests were used to evaluate the recovery of motor function upon cAMP administration and/or adenovirus-mediated gene transfer of AC5 in additional studies. The preliminary data were obtained from littermates of AC5KO, and WT males.

Results

Figure 8:
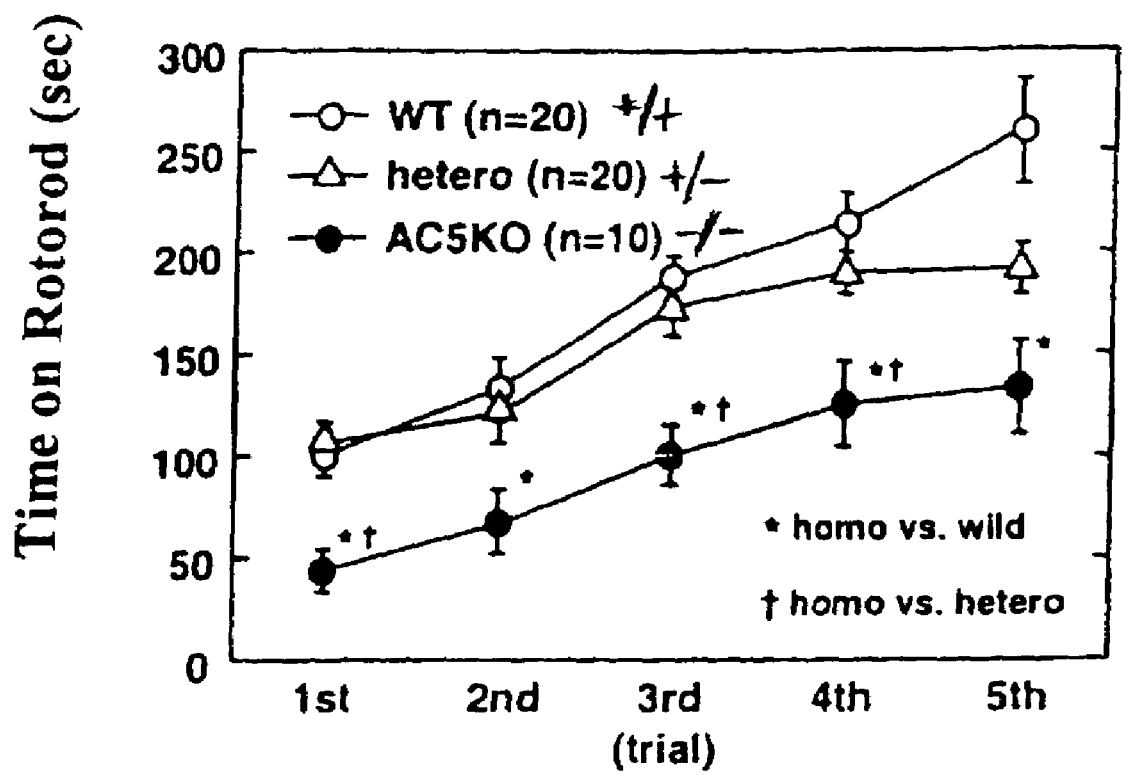
FIG. 8: Impaired rotor-rod performance in AC5KO mice: Three month old male were used (n=10 to 20). Data represent mean ±SEM of five trials.

The inventors examined whether the locomotor activity of the AC5KO mouse was impaired compared to a normal mouse. At a glance, the AC5KO mice appeared normal, i.e., they were not catatonic or rigid. However, standard behavior tests readily revealed that the AC5KO mice had a significant impairment in motor function. Inventors analyzed them with a rotor rod test in which mice were put on a rotor rod as shown below. In this task, animals had to make continuous adjustment in balance and posture to remain upright on a rod. The time that mice spent on the accelerating rotor-rod without falling was measured. The rod increased from 3 rpm to 30 rpm during each 5-min trial. Each mouse went through 5 trials, which showed a gradual increase in the time on a rod showing "learning effects." There was no significant difference between WT and heterozygous (Hetero) mice at the $1^{st}$ through $4^{th}$ trial. At the $5^{th}$ trial, there was a small, but significant decrease in their performance in heterozygous mice. AC5KO, in contrast, showed a significant impairment at the $1^{st}$ trial and constantly had a shorter time on a rotor rod with poor learning effect, suggesting that the locomotor activity in AC5KO was significantly impaired (FIG. 8).

Figure 11:
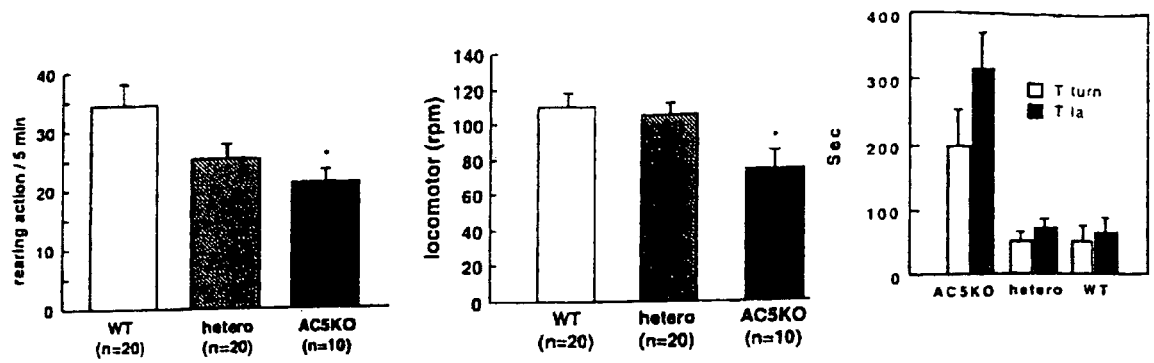
FIG. 11: Rearings (left), locomotor (middle) and pole test (right) in AC5KO, hetero and WT.[:] Male mice of 3 month old were used from each group (n=10-20)*p<0.01.

Horizontal and vertical spontaneous movements were not different between WT and Hetero, but greatly reduced in AC5KO (FIG. 11, left and middle). Similarly, the pole test showed that AC5KO had marked deficits in this test; they showed an over 3-fold prolongation of both recording time indexes (FIG. 11, right).

Thus, AC5KO had a significantly altered phenotype in motor function and mimicked Parkinson's disease, which is most likely caused by the loss of cAMP signal in the striatum, which was demonstrated in the AC assays. Another disease that may develop motor dysfunction is Huntington's disease. Huntington's disease is an inherited neurodegenerative disorder characterized by progressive motor, psychiatric, and cognitive disturbance. The motor disturbance begins subtly in human, as minor adventitious movements, and gradually progresses until the entire body is consumed in flagrant chorea and uncontrolled writhing, leading to death in human. This disease pathology is characterized by specific neurodegeneration of the striatum. Because the primary lesion in AC5KO is in the striatum, it was thought that the mice might have a phenotype of Huntington's disease, rather than Parkinson's disease. Inventors thus examined whether the mouse model had a neurological phenotype, such as a progressive clasping of the limbs, which can be readily triggered by a tail suspension test in the Huntington's disease model animals. Mice were suspended by the tail for 15s and videotaped for a tail suspension test. Animals were assessed for clasping score and clasping duration. An abnormal movement is defined as any dystonic movement of the hindlimbs, or a combination of hind- and forelimbs and trunk, during which the limbs may be pulled into the body in a manner not observed in normal mice. Our results showed that, however, AC5KO did not exhibit Huntington-like catatonic response, in repeated experiments (NS, n=20).

In summary, the loss of AC5 led to two major changes in the striatum; the loss of striatal AC activity as expected since this is the major striatal AC isoform although the magnitude of its loss (80%) was greater than what inventors originally anticipated. The second was, however, somewhat unexpected; it led to the Parkinson-like attenuation of motor function without inducing Huntington-like dysfunction. Thus, the disruption of AC5 caused not only a simple loss in enzymatic activity, but a loss in striatal function.

Inventors then examined if there were compensatory increases in the expression of the other AC isoforms in AC5KO. The inventors quantitated the mRNA expression of the AC isoforms by RNase protection assay. cRNA of the 28S ribosomal RNA was used as an internal control. In the striatum, AC1, AC3, AC5, AC6, AC8, and AC9 were readily detected while AC2, AC4 and AC7 were hardly detectable. Importantly, the expression of these isoforms was not different between AC5KO and WT. AC5 was abundantly expressed in WT, but not detected in AC5KO. Inventors also found that AC5 was most dominantly expressed in the striatum and was expressed at low levels in the cortex and hippocampus. AC5 expression was negligible in the cerebellum. For comparison, inventors had similar findings in the heart. AC5 expression was ablated in the absence of any compensatory increases in the other AC isoforms including AC6, indicating that AC5 expression was not compensated by an increase of its most relevant isoform expression (AC6).

Figure 10:
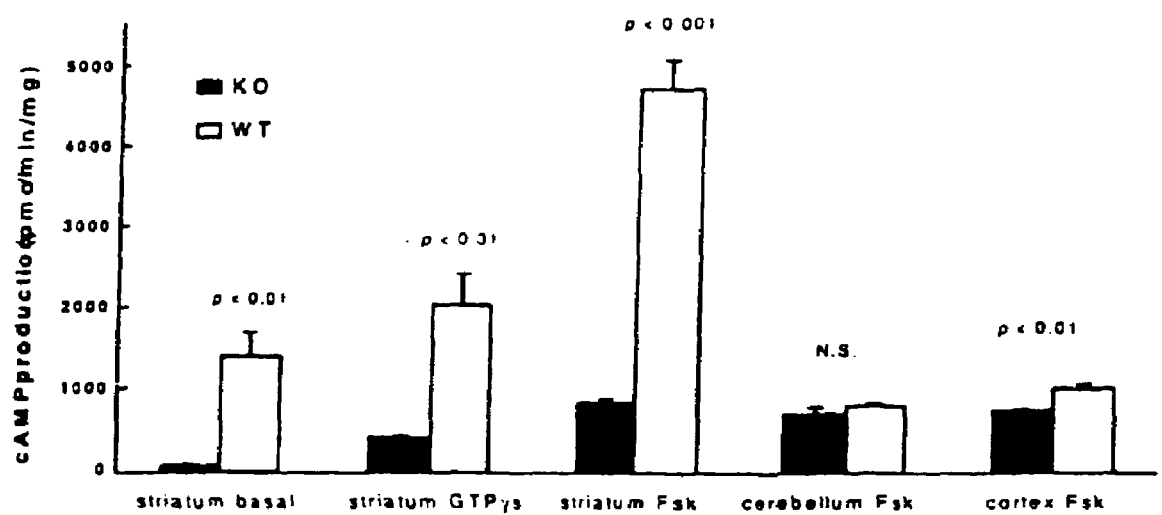
FIG. 10: AC activity in AC5KO. The steady state AC activity in the striatum (basal, GTPgammaS, and forskolin) and the cerebellum (forskolin), and the cortex (forskolin) were determined. Stimulation was performed at the level of G protein (100 micro M GTPgammaS) and AC (100 micro M forskolin).

Inventors then examined cAMP production in membranes from the striatum of AC5KO and WT at 2 month of age. The results are shown in FIG. 10. AC activity was decreased in the striatum relative to that in WT by approximately 80%, indicating that AC5 is the major isoform. In contrast, AC activity was significantly, but to a small degree, decreased in the cortex where AC5 could be detected in WT and showed no difference in the cerebellum by 25% where AC5 was scarcely expressed in WT. These findings confirmed the dominant expression of AC5 in the striatum, but not in the cortex or cerebellum.

Figure 12:
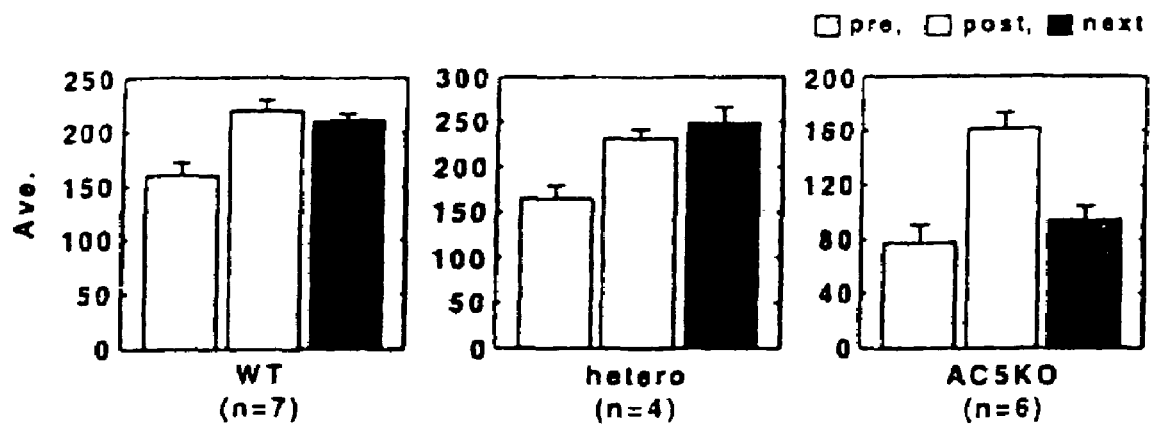
FIG. 12: Effects of db-cAMP on rotor-rod test.: Tests were performed before (pre), 30 minutes after (post), and 48 hours after (next) the injection of db-cAMP to WT, hetero and AC5KO (n=4-7).

Upon examination of the effects of cAMP analogs, such as db-cAMP, on motor function in WT, heterozygous or AC5KO mice, the preliminary experiment demonstrated that the time that mice spent on the rod without falling increased 30 minutes after db-cAMP injection; this is most likely a result from habituation or learning effect (FIG. 12). However, the magnitude of improvements was greater in AC5KO (approximately two-fold increase) than heterozygous (25% increase) and WT (30% increase). When the rotor rod performance was evaluated 48 hours after injection, the performance dropped to the basal level in AC5KO, while it remained similar in heterozygous and WT, the latter may be due to remaining habituation. Thus, we predict that the intraperitoneal injection of db-cAMP may improve motor activity, but only transiently and modestly. Similarly, L-dopa and cabergoline administration may improve motor function. Effect of oral administration of these drugs may be greater than that of intraperitoneal injection of db-cAMP because of better drug delivery to the striatum.

The disruption of AC5 may lead to a change in expression of receptors and neurotransmitters involved in cAMP signal and the neurons of the striatum, such as D1, D2, A2a, M1 receptors, the enkephalin/dynorphin, substance P, various G protein subunits, PKA, and CREB. In addition, cAMP content will be modified which leads to a loss of motor function and suggests a treatment including direct administration of cAMP or cAMP analogs such as L-dopa or cabergoline.

Figure 9:
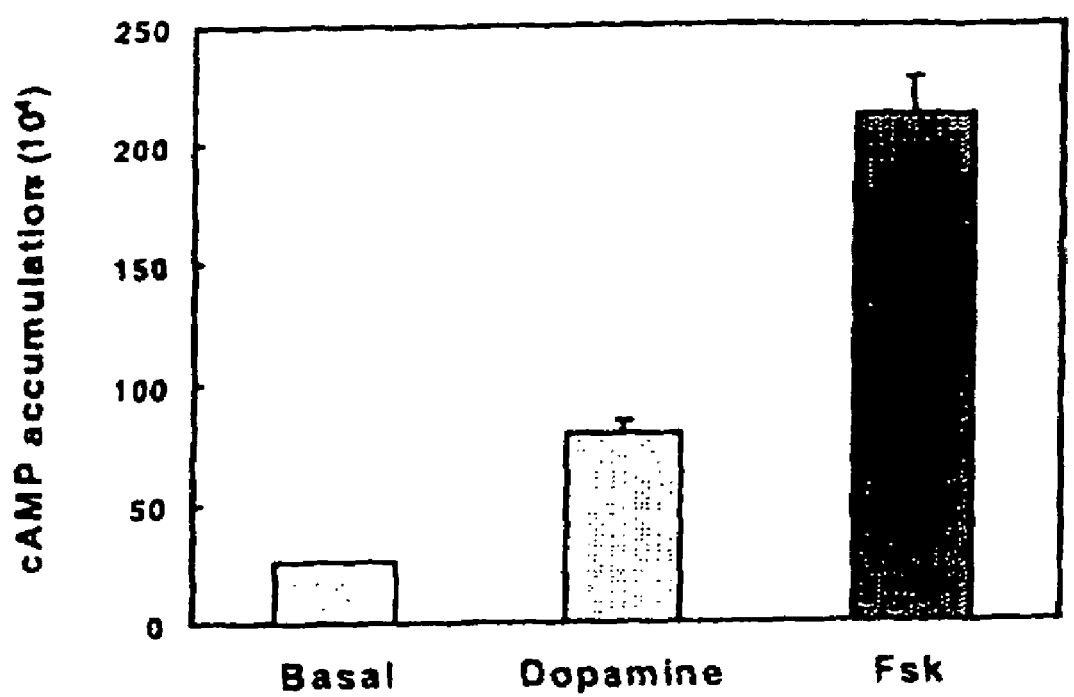
FIG. 9: cAMP production in primary cultured striatal neurons.: Forskolin (50 micro M) and dopamine (100 micro M) stimulated cAMP accumulation was measured (Mean ±SEM, n=4).

To determine whether D1 agonists such as dopamine or forskolin could have an effect on stimulation of AC5 activity, with the result being an increase in cAMP and improvement in neuronal function, neuronal cells from WT mice were treated with either dopamine or forskolin to determine if they could increase production of cAMP. As shown in FIG. 9, both dopamine and forskolin were effective at increasing the levels of cAMP significantly compared to untreated cells.

Example 4

Disruption of Type 5 AC Gene Preserves Cardiac Function Against Pressure Overload Chronic pressure overload is a cause of heart failure. In response to pressure overload, the myocardium undergoes adaptive hypertrophy in order to maintain cardiac output against the increased afterload. Prolonged pressure overload eventually leads to heart failure as reflected by the dilatation of the left ventricle (LV) and a decrease in cardiac contractility, eg. left ventricular ejection fraction (LVEF). Pressure overload also results in apoptosis, which is thought to be part of the mechanism of cardiac decompensation. The role of the beta adrenergic (β-AR) signaling pathway is well defined as a primary defense against acute stress or changes in hemodynamic load; however, uncertainty remains about its role in the pathogenesis of heart failure. The purpose of the experiment below was to examine the effects of chronic pressure overload induced by aortic banding in AC5KO and WT controls. Specifically, the extent to which LV hypertrophy and apoptosis developed in response to pressure overload and the resultant effects on cardiac function were examined.

Aortic Banding

Transverse aortic banding or sham operation was performed in 4-6 month-old homozygous AC5KO and WT littermates. The method of imposing pressure overload in mice has been described in other work. Mice were anesthetized intraperitoneally with a mixture of ketamine (0.065 mg/g), xylazine (0.013 mg/g), and acepromazine (0.002 mg/g). Mice were ventilated via intubation with a tidal volume of 0.2 ml and a respiratory rate of 110 breaths per minute. The left side of the chest was opened at the second intercostal space and the transverse thoracic aorta was constricted. To measure the pressure gradient across the constriction, two high-fidelity catheter tip transducers (1.4 F; Millar Instruments Inc.) were used at one week after aortic banding. One was inserted into the right carotid artery and the other into the right femoral artery, and they were advanced carefully to the ascending aorta and abdominal aorta, respectively, where pressures were measured simultaneously.

Echocardiography

Mice were anesthetized as already discussed. Echocardiography was performed using ultrasonography (Sequoia C256; Acuson Corporation) (Iwase, M. et al. (1996), Circ. Res. 78:517-524; Iwase, M. et al. (1997), Am. J. Physiol. 272, H585-H589). A dynamically focused 13 MHz annular array transducer was applied from below, using a warmed saline bag as a standoff. M-mode measurements of LV internal diameter were made from more than three beats and averaged. Measurements of the LV end-diastolic diameter (LVEDD) were taken at the time of the apparent maximal LV diastolic dimension, while measurements of the LV end-systolic diameter (LVESD) were taken at the time of the most anterior systolic excursion of the posterior wall. LVEF was calculated by the cubic method: LVEF (%)=[(LVEDD)$^3$−(LVESD)$^3$]/(LVEDD)$^3$.

Evaluation of Apoptosis

DNA fragmentation was detected in situ by using TUNEL staining (Asai, K. et al. (1999), J. Clin. Invest. 104: 551-558). Briefly, deparaffinized sections were incubated with proteinase K and DNA fragments labeled with biotin-conjugated dUTP and terminal deoxyribonucleotide transferase and visualized with FITC-ExtrAvidin (Sigma-Aldrich). Nuclear density was determined by manual counting of 4', 6-diamidine-2'-phenylindole dihydrochloride (DAPI)-stained nuclei in six fields of each animal using the x40 objective, and the number of TUNEL-positive nuclei was counted by examining the entire section using the same power objective. Limiting the counting of total nuclei and TUNEL-positive nuclei to areas with a true cross section of myocytes made it possible to selectively count only those nuclei that were clearly within myocytes. For some samples, triple staining with propidium iodide (Vector Laboratories Inc.), TUNEL, and anti-α-sarcomeric actin antibody (Sigma-Aldrich), and subsequent analyses using confocal microscopy, were performed in order to verify the results obtained with light microscopy.

Myocyte Cross-Sectional Area

Myocyte cross-sectional area was measured from images captured from silver-stained 1-μm-thick methacrylate sections. Suitable cross sections were defined as having nearly circular capillary profiles and circular-to-oval myocyte sections. No correction for oblique sectioning was made. The outline of 100-200 myocytes was traced in each section. MetaMorph image system software (Universal Imaging Corp.) was used to determine myocyte cross-sectional area.

Western Blotting

Crude cardiac membrane fractions were prepared and separated on 4-20% SDS-polyacrylamide gel and blotted onto nitrocellulose membrane. Western blotting was conducted with anti-Bcl-2 and anti-Bax antibodies (BD Biosciences). Expression of these proteins was quantified by densitometry.

RNase Protection Assay

Total mRNA in the heart was prepared, and the amount of mRNA of Bcl-2 was determined by RNase protection assay using RPA III kit (Ambion). To probe Bcl-2, a partial fragment of mouse Bcl-2 gene was obtained by RT-PCR. A human 18S rRNA probe was used as an internal control. The relative intensity of Bcl-2 to 18S rRNA was quantified by densitometry.

Statistical Analysis

All data are reported as mean ±SEM. Comparisons between AC5KO and WT values were made using Student's t-test. For statistical analysis of data from multiple groups, ANOVA was used. $P<0.05$ was taken as a minimal level of significance.

Results

Disruption of Type 5AC did not Affect the Development of Cardiac Hypertrophy

Figure 13:
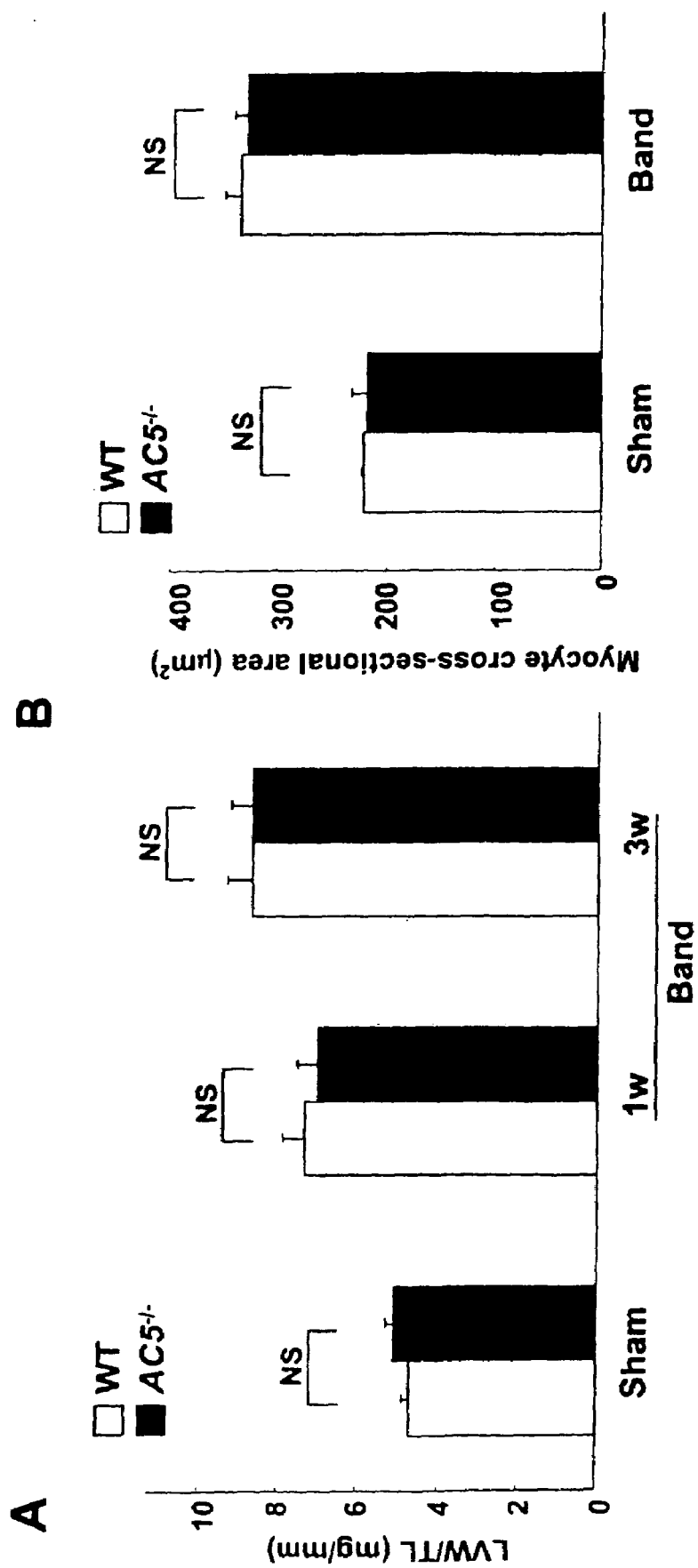
FIGS. 13A and B: Comparison of cardiac hypertrophy after aortic banding in WT and AC5−/− mice.

At baseline, there was no difference between WT and AC5KO in the LV weight (LVW; mg)/tibial length (TL; mm) (WT 4.7±0.2, AC5KO 5.1±0.2 mg/mm, n=9-14, P=NS). The time course and the degree of the development of cardiac hypertrophy (LVW/TL) in response to pressure overload were similar between WT and AC5KO (FIG. 13A). LVW/body weight, another index of cardiac hypertrophy, confirmed the data from LVW/TL (data not shown). Myocyte cross-sectional area, another index of hypertrophy, increased similarly in both WT and AC5KO at 3 weeks of banding, confirming the gross pathological data (FIG. 13B).

Cardiac Function was Preserved in AC $\%^{-/-}$ after 3 Weeks of Aortic Banding

Figure 14:
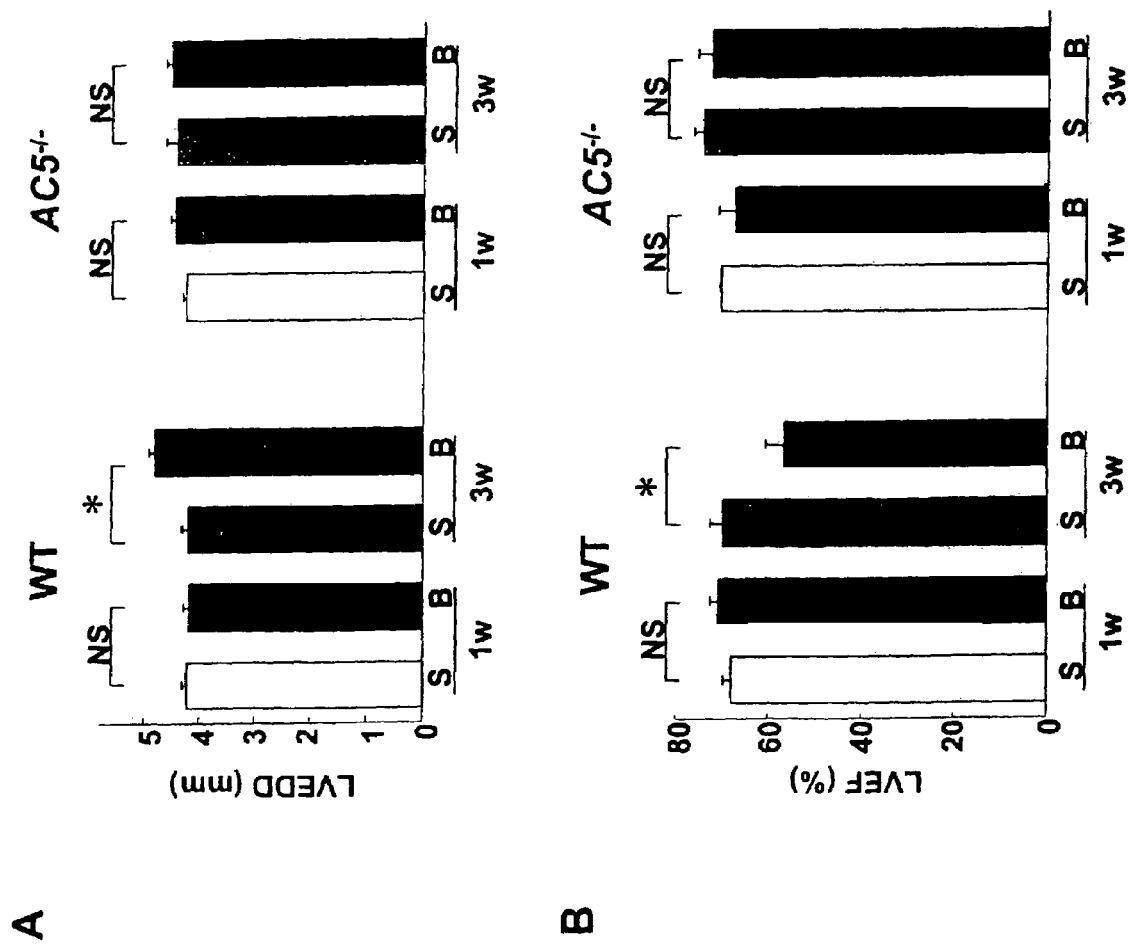
FIGS. 14A and B: Changes in LV function after banding in WT and AC5−/− mice

LV dimensions and cardiac function were evaluated echocardiographically. There was no difference in LVEDD and LVEF between WT and AC5KO at baseline and a 1 week after banding when they were compared to each other or to sham-operated animals (FIG. 14). At 3 weeks after banding, however, LVEDD was significantly increased in WT, while it remained unchanged in AC5KO (FIG. 14A). Similarly, LVEF fell significantly from 70±2.8 to 57±3.9% (P<0.05, n=8-11) in WT, while it remained unchanged at 74±2.2% in AC5KO (FIG. 14B). These results suggest that cardiac function was protected following chronic pressure overload in AC5KO. This was not due to a difference in pressure gradient, which was similar at 1 week after banding in AC5KO (102±8.2 mmHg) vs. WT (112±3.1 mmHg). Heart rate was not significantly different in WT and AC5KO under anesthesia during echocardiography, but was elevated in the conscious state in AC5KO.

Apoptosis was Protected in AC5KO at 1 Week of Banding.

Figure 15:
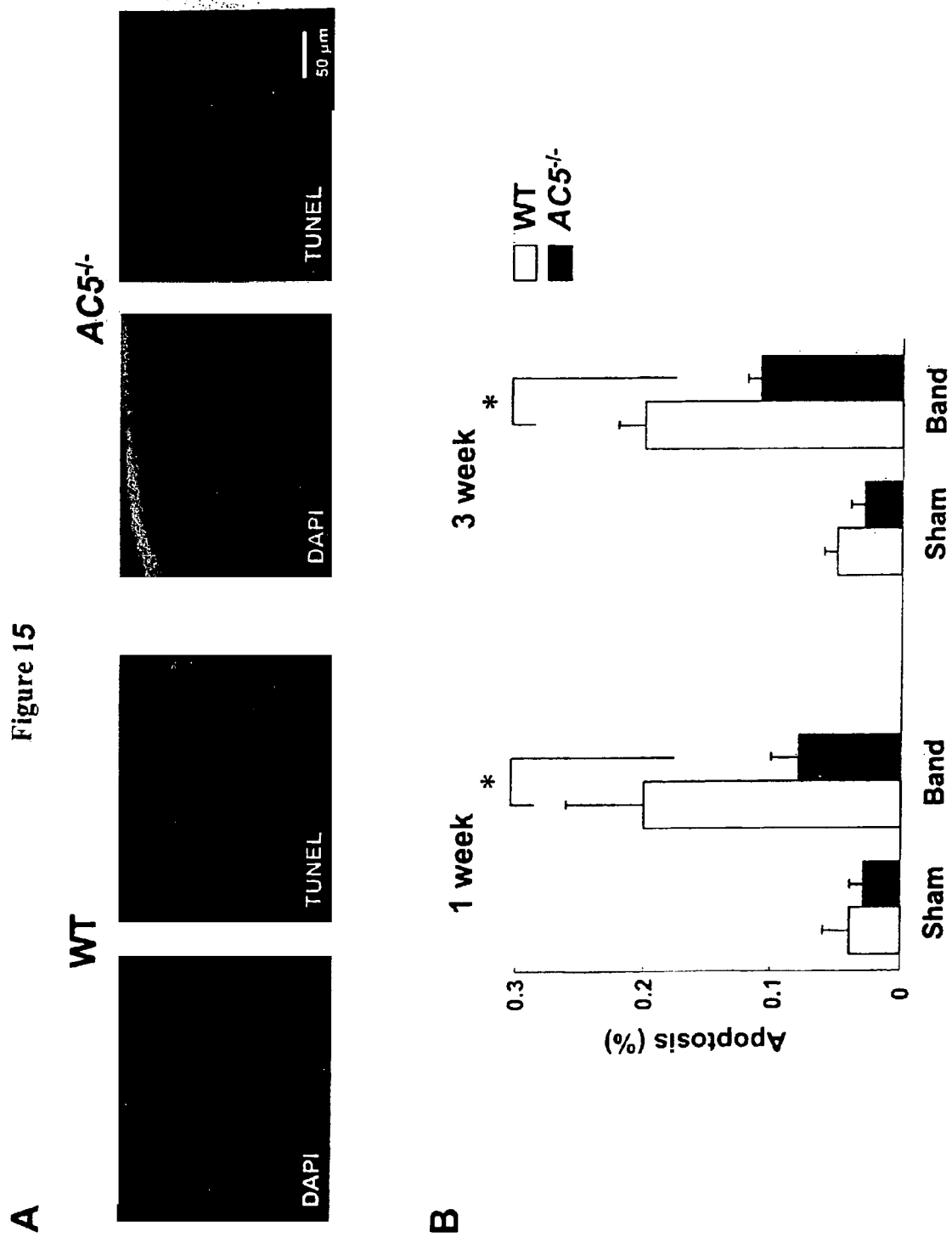
FIGS. 15A and B: Comparison of TUNEL staining after banding between WT and AC5−/− mice FIGS. 16A and B: Western Blotting and RNase protection assay of Bcl-2 after banding in WT and AC5−/− mice.

Before banding, there was no difference in the number of TUNEL-positive cells between the two groups, suggesting that the lack of type 5 AC did not alter the viability of cardiac myocytes at baseline. Aortic banding increased the number of TUNEL-positive cells in WT roughly 4-fold, at both 1 and 3 weeks after aortic banding (FIGS. 15A & B)). The increase in apoptosis was roughly half that of WT at 3 weeks and less at 1 week after banding (FIGS. 15 A & B).

Figure 16:
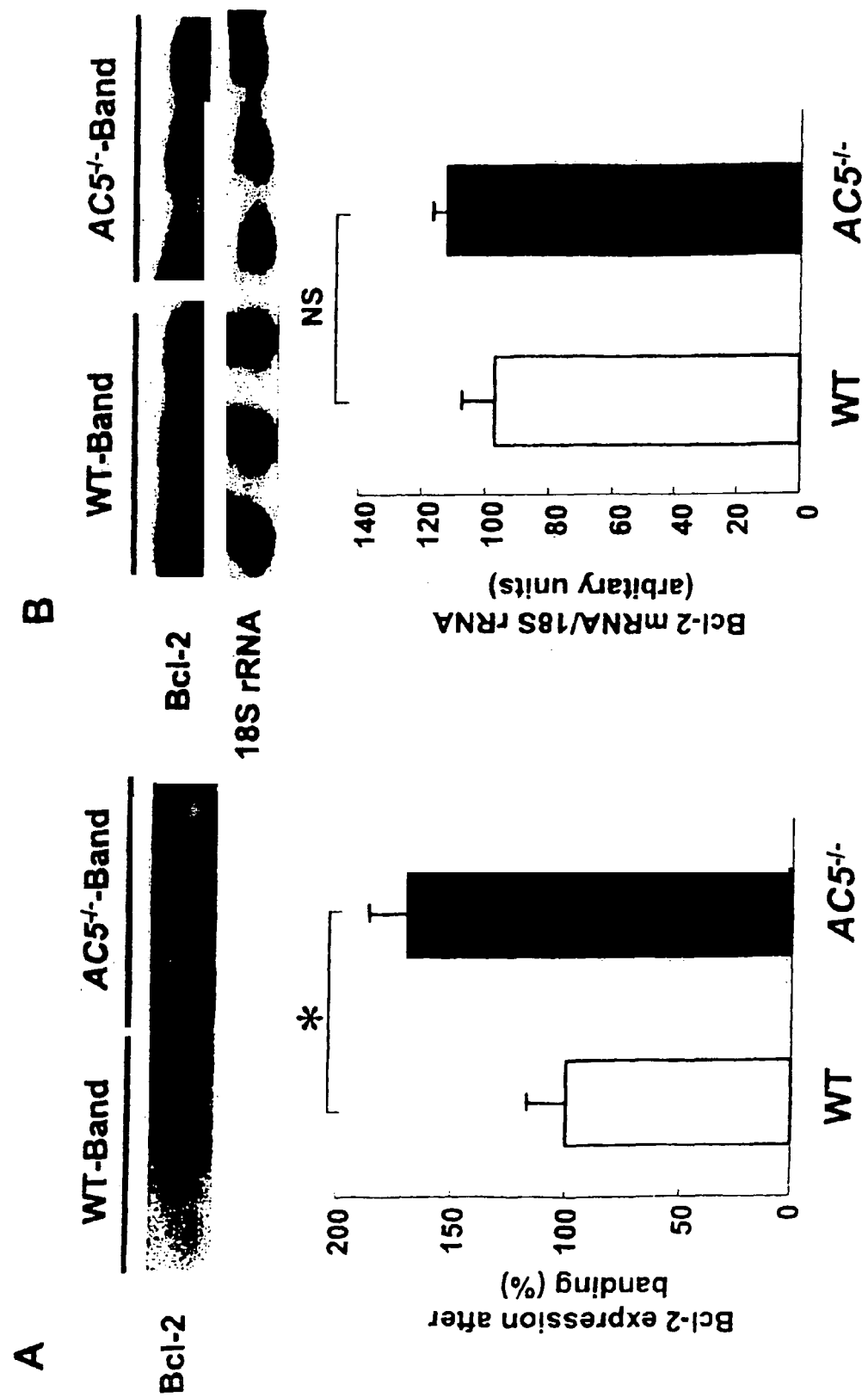

Expression of Bcl-2 is Enhanced in AC5KO Hearts in Response to Pressure Overload To examine changes in the molecules that are involved in apoptosis signaling, the inventors quantitated Bcl-2, an inhibitor of apoptosis, and Bax, an accelerator of apoptosis, in WT and AC5KO (FIG. 16). Bcl-2 expression was hardly detectable in the sham groups (data not shown). Interestingly, Bcl-2 protein expression was upregulated after 3 weeks of banding in both WT and AC5KO, although the magnitude of the increment was greater, P<0.05, in AC5KO (FIG. 16A). On the other hand, Bax expression was not different in the sham and banded groups (data not shown). The mRNA expression of Bcl-2 was also examined. In parallel with Bcl-2 protein, mRNA of Bcl-2 was upregulated after 3 weeks of banding in both WT and AC5KO, but the magnitude of the increment was not different between WT and AC5KO (FIG. 16B). These results suggest that the apoptotic process is attenuated, at least in part, through the post-transcriptional regulation of Bcl-2 in AC5KO hearts.

We claim:

1. A monoclonal antibody to adenylyl cyclase 5, wherein said antibody is characterized by its ability to specifically bind to adenylyl cyclase 5, but does not bind to or cross react with adenylyl cyclase 6 or to any other adenylyl cyclase, and wherein said monoclonal antibody is 19D5.C1 produced by a hybridoma having ATCC accession number PTA-5880.

2. A hybridoma having ATCC accession number PTA-5880 that produces a monoclonal antibody capable of specifically binding adenylyl cyclase 5 (AC5).

* * * * *

UNITED STATES PATENT AND TRADEMARK OFFICE
CERTIFICATE OF CORRECTION

| | | |
|---|---|---|
| PATENT NO. | : 8,263,401 B2 | Page 1 of 1 |
| APPLICATION NO. | : 11/597065 | |
| DATED | : September 11, 2012 | |
| INVENTOR(S) | : Stephen F. Vatner | |

It is certified that error appears in the above-identified patent and that said Letters Patent is hereby corrected as shown below:

On the Title Page, please insert -- Related U.S. Application Data --

At Item (60), please insert -- Provisional application No. 60/574,660, filed on May 26, 2004. --

Signed and Sealed this
Twenty-ninth Day of January, 2013

David J. Kappos
*Director of the United States Patent and Trademark Office*

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)...(1)
<223> OTHER INFORMATION: acetylated glycine
<220> FEATURE:
<221> NAME/KEY: MOD_RES
<222> LOCATION: (21)...(21)
<223> OTHER INFORMATION: amidated cysteine
```

```
<400> SEQUENCE: 1

Gly Asn Gln Val Ser Lys Glu Met Lys Arg Met Gly Phe Glu Asp Pro
1               5                   10                  15

Lys Asp Lys Asn Cys
            20
```